(12) United States Patent
Iwakuma et al.

(10) Patent No.: US 8,580,391 B2
(45) Date of Patent: *Nov. 12, 2013

(54) MATERIAL FOR ORGANIC ELECTROLUMINESCENCE DEVICES AND ORGANIC ELECTROLUMINESCENCE DEVICE USING THE MATERIAL

(75) Inventors: Toshihiro Iwakuma, Sodegaura (JP); Hiroshi Yamamoto, Sodegaura (JP); Yoshio Hironaka, Sodegaura (JP); Hidetsugu Ikeda, Sodegaura (JP); Chishio Hosokawa, Sodegaura (JP); Seiji Tomita, Sodegaura (JP); Takashi Arakane, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 1084 days.

This patent is subject to a terminal disclaimer.

(21) Appl. No.: 11/150,342

(22) Filed: Jun. 13, 2005

(65) Prior Publication Data

US 2005/0249976 A1  Nov. 10, 2005

Related U.S. Application Data

(63) Continuation of application No. 10/393,988, filed on Mar. 24, 2003, now abandoned.

(30) Foreign Application Priority Data

Mar. 22, 2002 (JP) ................................. 2002-081234
Oct. 15, 2002 (JP) ................................. 2002-299810

(51) Int. Cl.
*H01L 51/54* (2006.01)
*C09K 11/06* (2006.01)
*C07D 403/00* (2006.01)

(52) U.S. Cl.
USPC ........... 428/690; 428/917; 313/504; 313/506; 257/E51.05; 544/296; 544/333; 548/440

(58) Field of Classification Search
None
See application file for complete search history.

(56) References Cited

U.S. PATENT DOCUMENTS

| | | | |
|---|---|---|---|
| 6,242,115 B1 | 6/2001 | Thomson et al. | |
| 6,824,891 B2 | 11/2004 | Okada et al. | |
| 7,990,046 B2* | 8/2011 | Iwakuma et al. | ............. 313/504 |
| 2002/0055014 A1 | 5/2002 | Okada et al. | |
| 2003/0218418 A9* | 11/2003 | Sato et al. | ............. 313/504 |
| 2005/0127823 A1* | 6/2005 | Iwakuma et al. | ............. 313/504 |
| 2005/0249976 A1 | 11/2005 | Iwakuma et al. | ............. 428/690 |

FOREIGN PATENT DOCUMENTS

| | | |
|---|---|---|
| EP | 0 926 216 | 6/1999 |
| EP | 1 202 608 | 5/2002 |
| EP | 1 205 527 | 5/2002 |
| JP | 3-200889 | 9/1991 |
| JP | 7-138561 | 5/1995 |
| JP | 8-12600 | 1/1996 |
| JP | 8-239655 | 9/1996 |
| JP | 11-111460 | 4/1999 |
| JP | 2000-068059 | 3/2000 |
| JP | 2000-169448 | 6/2000 |
| JP | 2001-064640 | 3/2001 |
| JP | 2001-160489 | 6/2001 |
| JP | 2001-192653 | 7/2001 |
| JP | 2001-207167 | 7/2001 |
| JP | 2001-247858 | 9/2001 |
| JP | 2001-288462 | 10/2001 |
| JP | 2002-193952 | 7/2002 |
| JP | 2003-031371 | 1/2003 |
| JP | 4316387 B2 | 8/2009 |
| WO | WO 01/19939 | 3/2001 |
| WO | WO 01/72927 | 10/2001 |
| WO | WO 03/079736 A1 | 9/2003 |

OTHER PUBLICATIONS

Patent Abstracts of Japan, JP 2003-231692, Aug. 19, 2003.
Patent Abstracts of Japan, JP 2003-178884, Jun. 27, 2003.

* cited by examiner

*Primary Examiner* — Marie R. Yamnitzky
(74) *Attorney, Agent, or Firm* — Oblon, Spivak, McClelland, Maier & Neustadt, L.L.P.

(57) ABSTRACT

A material for organic electroluminescence devices comprising a compound in which a heterocyclic group having nitrogen is bonded to an arylcarbazolyl group or a carbazolylalkylene group and an organic electroluminescence device comprising an anode, a cathode and an organic thin film layer comprising at least one layer and disposed between the anode and the cathode, wherein at least one layer in the organic thin film layer comprises the material for organic electroluminescence devices described above. The material can provide an organic electro-luminescence device emitting bluish light with a high purity of color. The organic electroluminescence device uses the material.

25 Claims, No Drawings

MATERIAL FOR ORGANIC ELECTROLUMINESCENCE DEVICES AND ORGANIC ELECTROLUMINESCENCE DEVICE USING THE MATERIAL

This application is a continuation application of U.S. patent application Ser. No. 10/393,988 filed on Mar. 24, 2003 (now abandoned) and claims priority to Japanese Application Nos. 2002-081234 filed on Mar. 22, 2002 and 2002-299810 filed on Oct. 15, 2002, the entire contents of each of the above are hereby incorporated by reference.

TECHNICAL FIELD

The present invention relates to a material for organic electro-luminescence devices (organic EL devices) and an organic EL device using the material and, more particularly, to an organic EL device emitting bluish light with a high purity of color.

BACKGROUND ART

Organic EL devices which utilize organic substances are expected to be useful for application as an inexpensive full color display device of the solid light emission type having a great size and various developments on the organic EL devices are being conducted. In general, an organic EL device has a construction comprising a light emitting layer and a pair of electrodes disposed at both sides of the light emitting layer.

The light emission of the organic EL device is a phenomenon in which, when an electric field is applied between the two electrodes, electrons are injected from the cathode side and holes are injected from the anode side, the electrons are recombined with the holes in the light emitting layer to form an excited state, and energy generated when the excited state returns to the ground state is emitted as light.

As the light emitting material, chelate complexes such as tris(8-quinolinolato)aluminum, coumarine derivatives, tetraphenylbutadiene derivatives, bisstyrylarylene derivatives and oxadiazole derivatives are known. It has been reported that these light emitting materials emit light in the visible region of blue to red and it is expected that color display devices can be obtained by using these light emitting materials (for example, Japanese Patent Application Laid-Open Nos. Heisei 8(1996)-239655, and Heisei 7(1995)-138561.

Although the practical use of displays using organic EL devices recently started, the full color display device is still under development. In particular, an organic EL device which emits bluish light with excellent purity of color and efficiency of light emission has been desired.

As the device as the attempt to satisfy the above desire, for example, a device using a phenylanthracene derivative as the material emitting blue light is disclosed in Japanese Patent Application Laid-Open No. Heisei 8(1996)-12600. The phenylanthracene derivative is used as the material emitting blue light and, in general, used as a laminate composed of a layer of the material emitting blue light and a layer of a complex of tris(8-quinolinolato)aluminum (Alq). However, the efficiency of light emission, the life and the purity of blue light are insufficient for the practical application. In Japanese Patent Application Laid-Open No. 2001-288462, a device emitting blue light in which an amine-based aromatic compound is used for the light emitting layer is disclosed. However, the efficiency of light emission of this device is as insufficient as 2 to 4 cd/A. In Japanese Patent Application Laid-Open No. 2001-160489, a device in which an azafluoranthene compound is added to the light emitting layer is disclosed. However, this device emits light of yellow to green and cannot emit blue light having a sufficiently high purity of color.

DISCLOSURE OF THE INVENTION

The present invention is made to overcome the above problems and has an object of providing a material for organic EL devices which emits bluish light with excellent purity of color and an organic EL device utilizing the material.

As the result of extensive studies by the present inventors, it was found that an organic EL device exhibiting excellent purity of blue color could be obtained by using a compound having a heterocyclic group having nitrogen bonded to an arylcarbazolyl group or a carbazolylalkylene group as the host material. The present invention has been completed based on this knowledge.

The present invention provides a material for organic electroluminescence devices which comprises a compound represented by following general formula (1) or (2):

(1)

(2)

wherein Cz represents a substituted or unsubstituted arylcarbazolyl group or carbazolylalkylene group, A represents a group represented by following general formula (A):

(A)

wherein M and M' each independently represent a heteroaromatic ring having 2 to 40 carbon atoms and nitrogen atom and forming a substituted or unsubstituted ring, M and M' may represent a same ring or different rings, L represents a single bond, a substituted or unsubstituted aryl group or arylene group having 6 to 30 carbon atoms, a substituted or unsubstituted cycloalkylene group having 5 to 30 carbon atoms or a substituted or unsubstituted heteroaromatic ring having 2 to 30 carbon atoms, p represents an integer of 0 to 2, q represents an integer of 1 or 2, r represents an integer of 0 to 2, and p+r represents an integer of 1 or greater; and n and m each represent an integer of 1 to 3.

The present invention also provides an organic electroluminescence device comprising an anode, a cathode and an organic thin film layer comprising at least one layer and disposed between the anode and the cathode, wherein at least one layer in the organic thin film layer comprises a material for organic electroluminescence devices described above. Among the above organic thin film layers, the light emitting layer, the electron transporting layer or the hole transporting layer may comprise the above material for organic EL devices.

THE MOST PREFERRED EMBODIMENT TO CARRY OUT THE INVENTION

The material for organic electroluminescence devices of the present invention comprises a compound represented by following general formula (1) or (2):

(1)

(2)

In the above formulae, Cz represents a substituted or unsubstituted arylcarbazolyl group or carbazolylalkylene group and n and m each represent an integer of 1 to 3.

It is preferable that the aryl group in the arylcarbazolyl group has 6 to 30 carbon atoms. Examples of the aryl group include phenyl group, naphthyl group, anthryl group, phenanthryl group, naphthacenyl group, pyrenyl group, fluorenyl group, biphenyl group and terphenyl group. Among these groups, phenyl group, naphthyl group, biphenyl group and terphenyl group are preferable.

It is preferable that the alkylene group in the carbazolylalkylene group has 1 to 10 carbon atoms. Examples of the alkylene group include methylene group, ethylene group, propylene group, isopropylene group, n-butylene group, s-butylene group, isobutylene group, t-butylene group, n-pentylene group, n-hexylene group, n-heptylene group, n-octylene group, hydroxymethylene group, chloromethylene group and aminomethylene group. Among these groups, methylene group, ethylene group, propylene group, isopropylene group, n-butylene group, t-butylene group and n-pentylene group are preferable.

In general formulae (1) and (2), A represents a group represented by the following general formula (A):

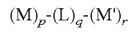

$(M)_p$-$(L)_q$-$(M')_r$ (A)

M and M' each independently represent a heteroaromatic ring having 2 to 40 carbon atoms and nitrogen atom and forming a substituted or unsubstituted ring, and M and M' may represent the same ring or different rings.

Examples of the heteroaromatic ring having nitrogen atom include rings of pyridine, pyrimidine, pyrazine, triazine, aziridine, azaindolidine, indolidine, imidazole, indole, isoindole, indazole, purine, puteridine, β-carboline, naphthylidine, quinoxaline, terpyridine, bipyridine, acridine, phenanthroline, phenazine and imidazopyridine. Among these rings, rings of pyridine, terpyridine, pyrimidine, imidazopyridine and triazine are preferable.

L represents a single bond, a substituted or unsubstituted aryl group or arylene group having 6 to 30 carbon atoms, a substituted or unsubstituted cycloalkylene group having 5 to 30 carbon atoms or a substituted or unsubstituted heteroaromatic ring having 2 to 30 carbon atoms.

p represents an integer of 0 to 2, q represents an integer of 1 or 2, r represents an integer of 0 to 2, and p+r represents an integer of 1 or greater.

Examples of the aryl group having 6 to 30 carbon atoms include phenyl group, biphenyl group, terphenyl group, naphthyl group, anthranyl group, phenanthryl group, pyrenyl group, chrysenyl group, fluoranthenyl group and perfluoroaryl groups. Among these groups, phenyl group, biphenyl groups, terphenyl group and perfluoroaryl groups are preferable.

Examples of the arylene group having 6 to 30 carbon atoms include phenylene group, biphenylene group, terphenylene group, naphthylene group, anthranylene group, phenanthrylene group, pyrenylene group, chrysenylene group, fluoranthenylene group and perfluroarylene groups. Among these groups, phenylene group, biphenylene group, terphenylene group and perfluoroarylene groups are preferable.

Examples of the cycloalkylene group having 5 to 30 carbon atoms include cyclopentylene group, cyclohexylene group and cycloheptylene group. Among these groups, cyclohexylene group is preferable.

Examples of the heteroaromatic group having 2 to 30 carbon atoms include 1-pyrrolyl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenoxazinyl group, 2-phenoxazinyl group, 1-phenothiazinyl group, 2-phenothiazinyl group, 3-phenothiazinyl group, 4-phenothiazinyl group, 10-phenothiaznyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group. Among these groups, pyridinyl group and quinolyl group are preferable.

Examples of the substituent in the group represented by Cz, M or M' in general formulae (1), (2) and (A) include halogen atoms such as chlorine atom, bromine atom and fluorine atom, carbazole group, hydroxyl group, substituted and unsubstituted amino groups, nitro group, cyano group, silyl group, trifluoromethyl group, carbonyl group, carboxyl group, substituted and unsubstituted alkyl groups, substituted and unsubstituted alkenyl groups, substituted and unsubstituted arylalkyl groups, substituted and unsubstituted aromatic groups, substituted and unsubstituted heteroaromatic heterocyclic groups, substituted and unsubstituted aralkyl groups, substituted and unsubstituted aryloxy groups and substituted and unsubstituted alkyloxyl groups. Among these groups, fluorine atom, methyl group, perfluorophenylene group, phenyl group, naphthyl group, pyridyl group, pyrazyl group, pyrimidyl group, adamantyl group, benzyl group, cyano group and silyl group are preferable.

The bonding mode of the compound represented by general formula (1) or (2) described above is shown in Table 1 in the following in accordance with the numbers represented by n and m.

TABLE 1

| n = m = 1 | n = 2 | n = 3 | m = 2 | m = 3 |
|---|---|---|---|---|
| Cz—A | Cz—A—Cz | Cz—A—Cz<br>\|<br>Cz | A—Cz—A | A—Cz—A<br>\|<br>A |

The bonding mode of the group represented by general formula (A) described above is shown in Table 2 in the following in accordance with the numbers represented by p, q and r.

TABLE 2

| No | p | q | r | The bonding mode |
|---|---|---|---|---|
| [1] | 0 | 1 | 1 | L—M' |
| [2] | 0 | 1 | 2 | L—M'—M', M'—L—M' |
| [3] | 0 | 2 | 1 | L—L—M', L—M'—L |
| [4] | 0 | 2 | 2 | L—L—M'—M', M'—L—L—M', L—M'—M'—L, M'—L—M', L—M'—L<br>(with L and M' branches) |
| [5] | 1 | 1 | 0 | The same as [1] except that M' is replaced with M. |
| [6] | 1 | 1 | 1 | M—L—M' |
| [7] | 1 | 1 | 2 | M—L—M'—M', M—L—M'<br>\|<br>M' |
| [8] | 1 | 2 | 0 | The same as [3] except that M' is replaced with M. |
| [9] | 1 | 2 | 1 | M—L—L—M', L—M—L—M', M—L—M'—L |
| [10] | 1 | 2 | 2 | M—L—L—M'—M', M'—L—M—L—M', M'—M'—L—M—L, M—L—L (with M' M' branches), M—L—L—M', L—L—M'—M', L—M—L—M', M—L—L (with M' branches) |
| [11] | 2 | 1 | 0 | The same as [2] except that M' is replaced with M. |
| [12] | 2 | 1 | 1 | The same as [7] except that M' is replaced with M and M is replaced with M'. |
| [13] | 2 | 1 | 2 | M—M—L—M'—M', M—L—M (with M' branches), M—L—M'—M' |
| [14] | 2 | 2 | 0 | The same as [4] except that M' is replaced with M. |
| [15] | 2 | 2 | 1 | The same as [10] except that M' is replaced with M and M is replaced with M'. |
| [16] | 2 | 2 | 2 | M—M—L—L—M'—M', M—M—L—M'—M', M—L—L—M'—M', M—L—L (with M' M' branches), M—M—L—L—M', L—L—M'—M', M—L—L—M (with M' branches) |

The group represented by Cz which is bonded to the group represented by A may be bonded to any of the groups represented by M, L or M' in general formula (A) representing the group represented by A.

For example, when the group represented by A has the bonding mode [6] in Table 2 (p=q=r=1) in the compound represented by Cz-A in which m=n=1 in general formula (1) or (2), the bonding mode includes three bonding modes of Cz-M-L-M', M-L(Cz)-M' and M-L-M'-Cz.

When the group represented by A has the bonding mode [7] in Table 2 (p=q=1 and r=2) in the compound represented by Cz-A-Cz in which n=2 in general formula (1), the bonding mode includes bonding modes shown in the following:

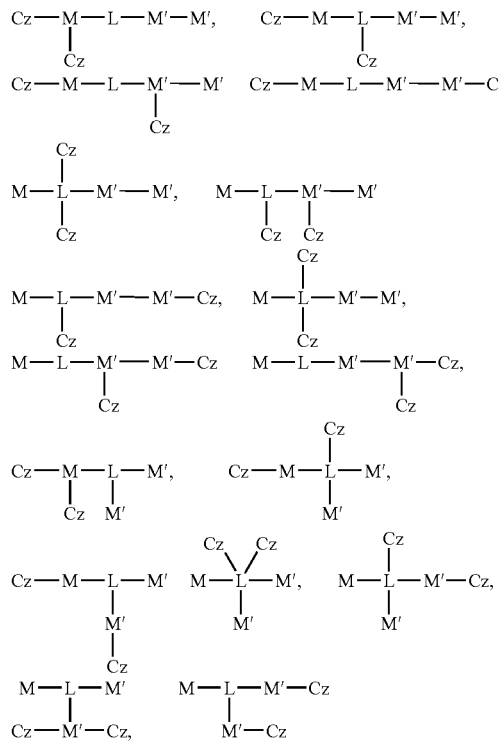

With respect to the bonding mode of the group represented by general formula (1), (2) or (A) and the combination of the groups shown in the above as the examples, materials for organic EL devices comprising compounds shown in (i) to (iv) in the following are preferable.

(i) Materials for organic EL devices in which
n=1 in general formula (1) and p=1 and r=0 in general formula (A);
in general formula (1), Cz represents a substituted or unsubstituted arylcarbazolyl group or carbazolylalkylene group; and
in general formula (A), M represents a heterocyclic six-membered or seven-membered ring having 4 or 5 carbon atoms and nitrogen atom and forming a substituted or unsubstituted ring, a heterocyclic five-membered ring having 2 to 4 carbon atoms and nitrogen atom and forming a substituted or unsubstituted ring, a heterocyclic ring having 8 to 11 carbon atoms and nitrogen atom and forming a substituted or unsubstituted ring or a substituted or unsubstituted imidazopyridinyl ring, and L represents a substituted or unsubstituted aryl group or arylene group having 6 to 30 carbon atoms or a substituted or unsubstituted heteroaromatic ring having 2 to 30 carbon atoms.

(ii) Materials for organic EL devices in which
n=2 in general formula (1) and p=1 and r=0 in general formula (A);
in general formula (1), Cz represents a substituted or unsubstituted arylcarbazolyl group or carbazolylalkylene group; and
in general formula (A), M represents a heterocyclic six-membered or seven-membered ring having 4 or 5 carbon atoms and nitrogen atom and forming a substituted or unsubstituted ring, a heterocyclic five-membered ring having 2 to 4 carbon atoms and nitrogen atom and forming a substituted or unsubstituted ring, a heterocyclic ring having 8 to 11 carbon atoms and nitrogen atom and forming a substituted or unsubstituted ring or a substituted or unsubstituted imidazopyridinyl ring, and L represents a substituted or unsubstituted aryl group or arylene group having 6 to 30 carbon atoms or a substituted or unsubstituted heteroaromatic ring having 2 to 30 carbon atoms.

(iii) Materials for organic EL devices in which
n=1 in general formula (1) and p=2 and r=0 in general formula (A);
in general formula (1), Cz represents a substituted or unsubstituted arylcarbazolyl group or carbazolylalkylene group; and
in general formula (A), M represents a heteroaromatic ring having 2 to 40 carbon atoms and nitrogen atom and forming a substituted or unsubstituted ring, and L represents a substituted or unsubstituted aryl group or arylene group having 6 to 30 carbon atoms or a substituted or unsubstituted heteroaromatic ring having 2 to 30 carbon atoms.

(iv) Materials for organic EL devices in which
m=2 in general formula (2) and p=q=1 in general formula (A);
in general formula (2), Cz represents a substituted or unsubstituted arylcarbazolyl group or carbazolylalkylene group; and
in general formula (A), M and M' each independently represent a heteroaromatic ring having 2 to 40 carbon atoms and nitrogen atom and forming a substituted or unsubstituted ring, and M and M' may represent a same ring or different rings, and L represents a substituted or unsubstituted aryl group or arylene group having 6 to 30 carbon atoms, a substituted or unsubstituted cycloalkylene group having 5 to 30 carbon atoms or a substituted or unsubstituted heteroaromatic ring having 2 to 30 carbon atoms.

In the above general formulae (1) and (2), it is preferable that Cz represents a substituted or unsubstituted arylcarbazolyl group and, more preferably, phenylcarbazolyl group. It is preferable that the aryl portion of the arylcarbazolyl group is substituted with carbazolyl group.

Specific examples of the compound represented by general formula (1) are shown in the following. However, the compound represented by general formula (1) is not limited to these compounds.

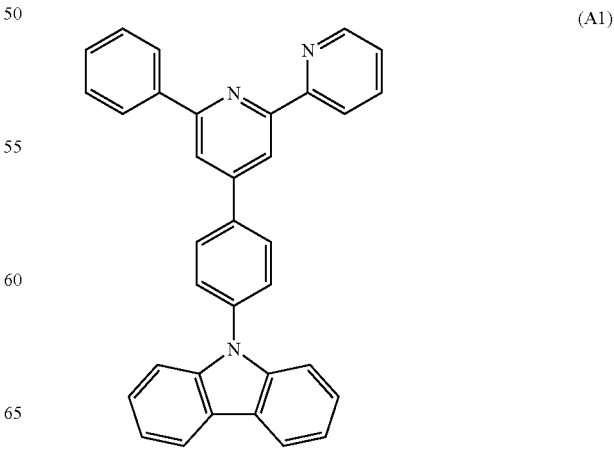

(A1)

-continued
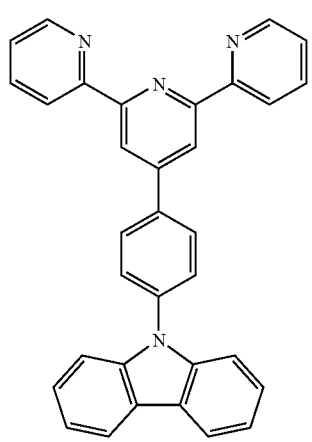
(A2)
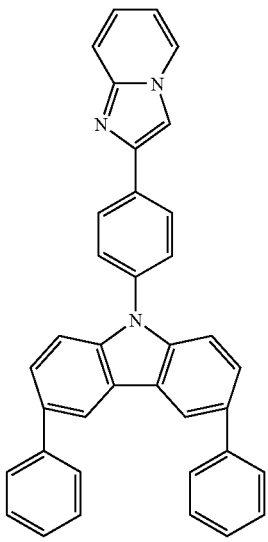
(A5)
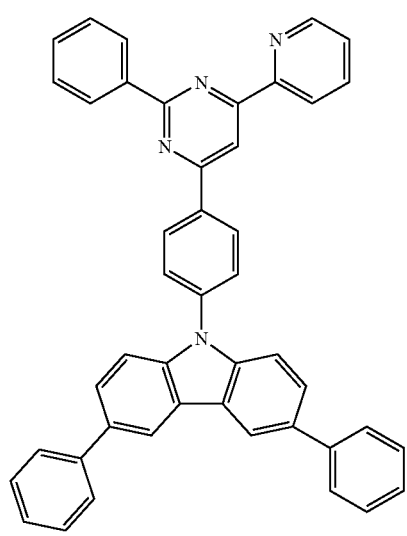
(A3)
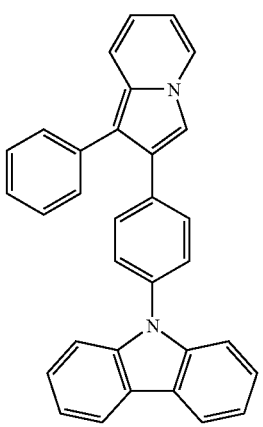
(A6)
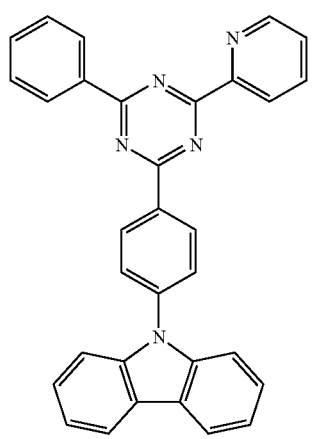
(A4)
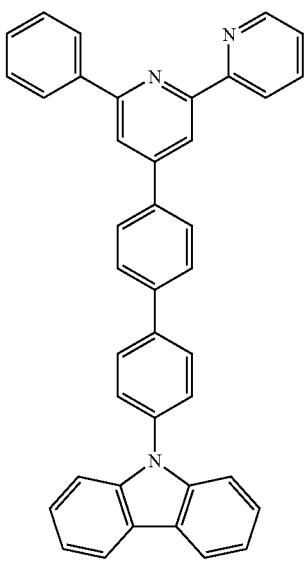
(A7)

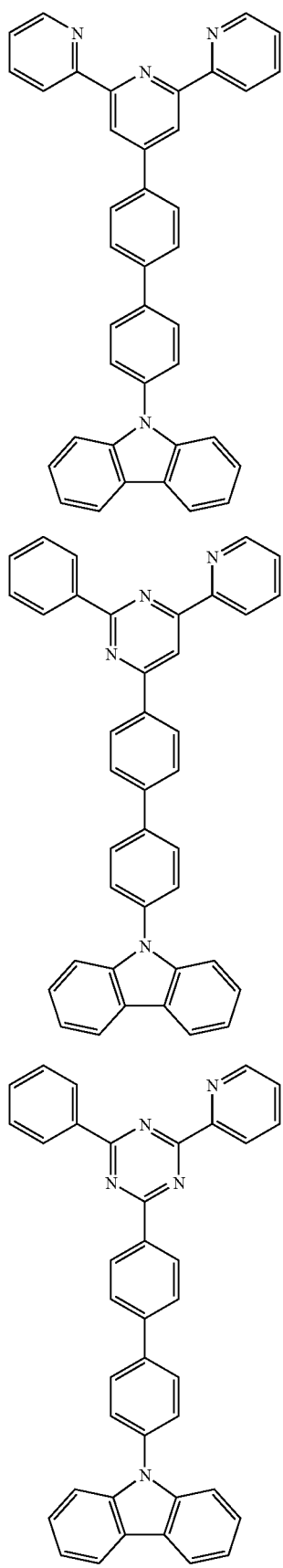
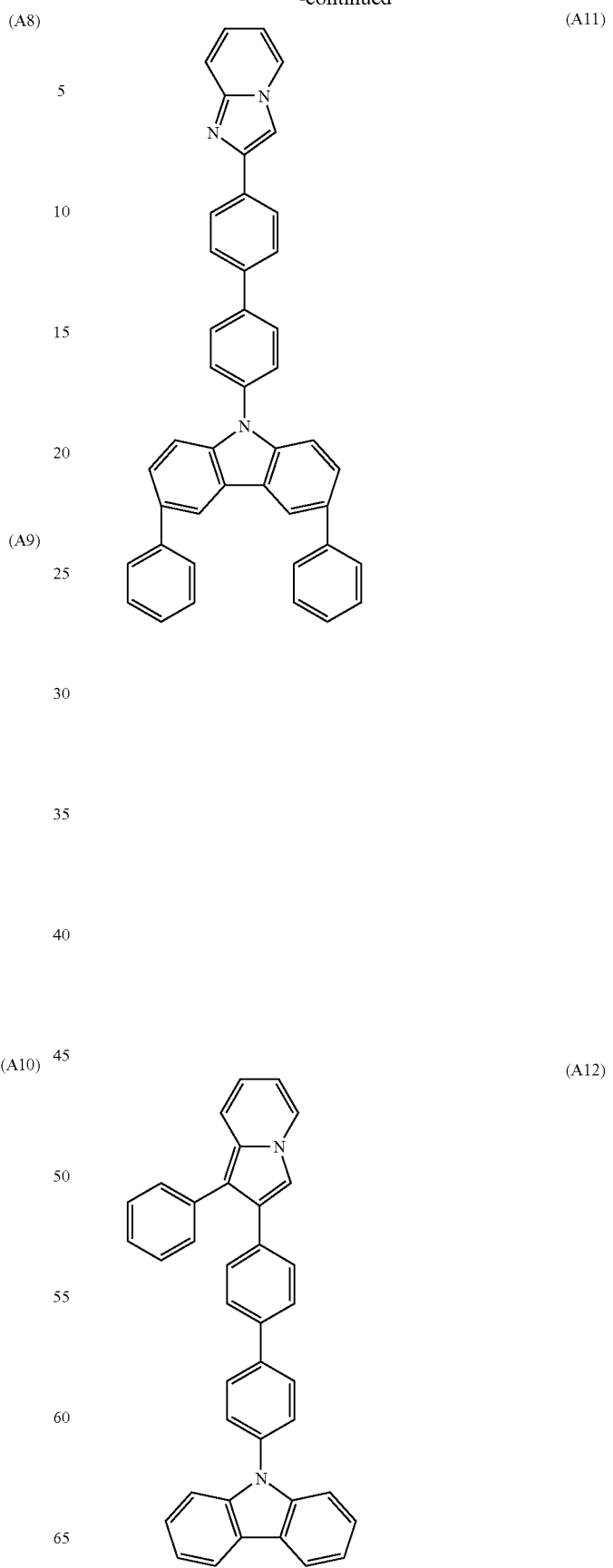

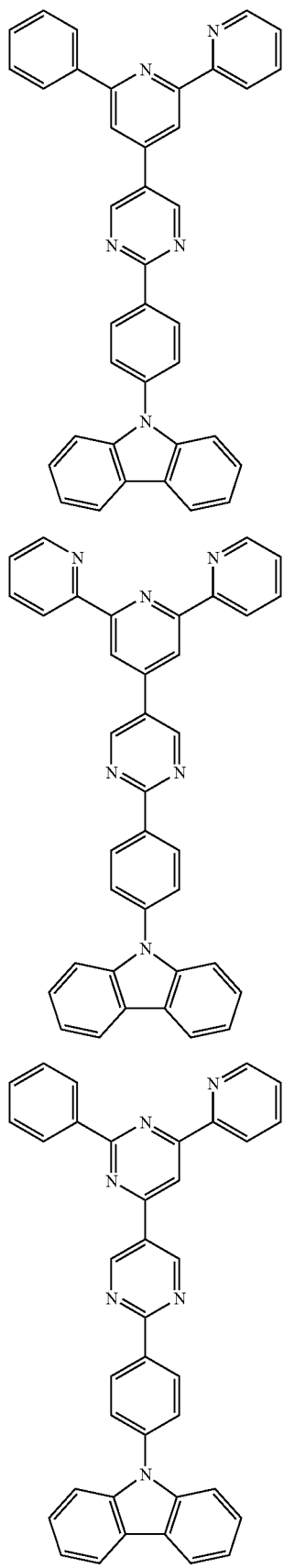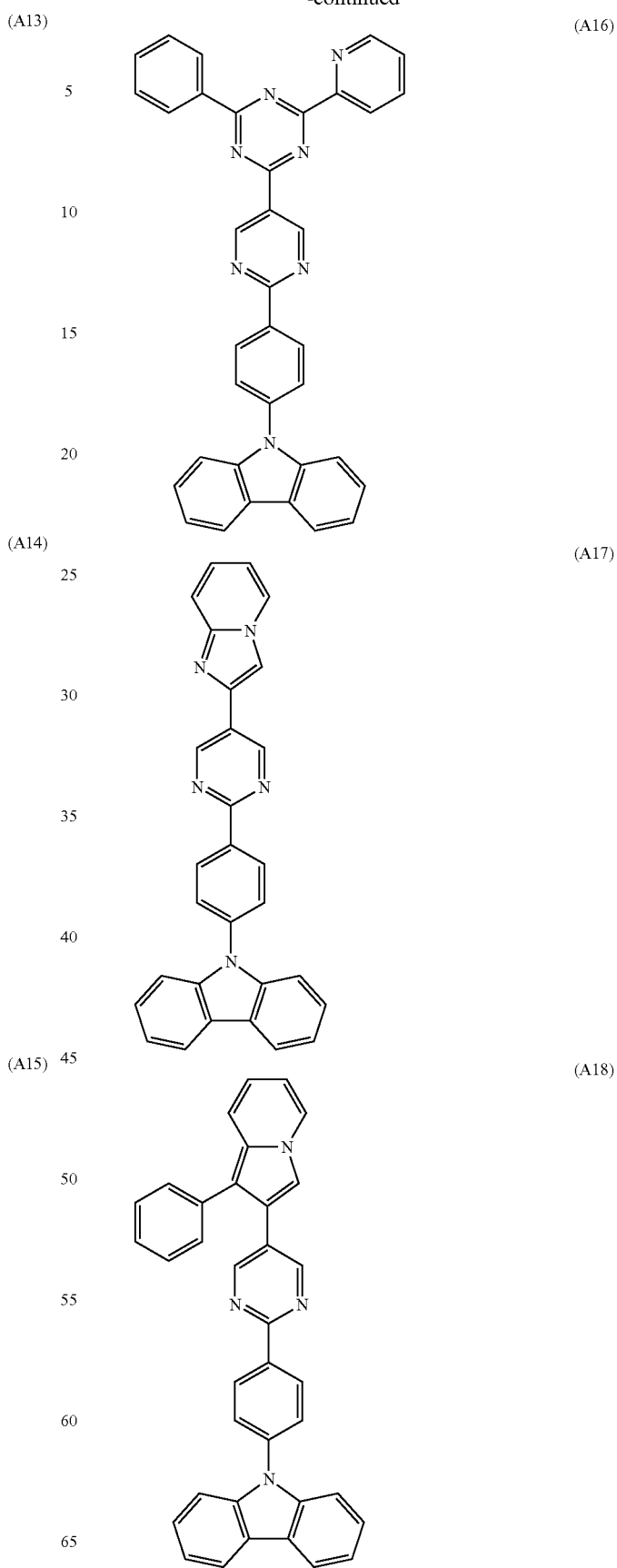

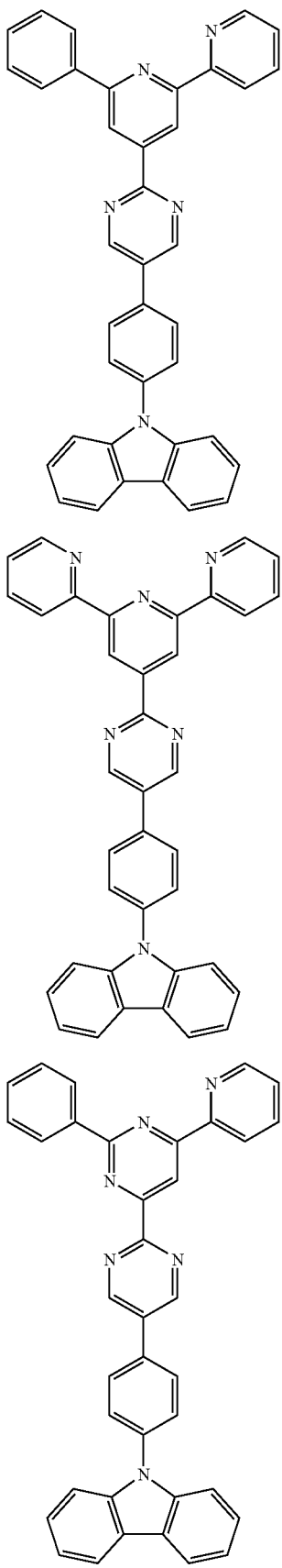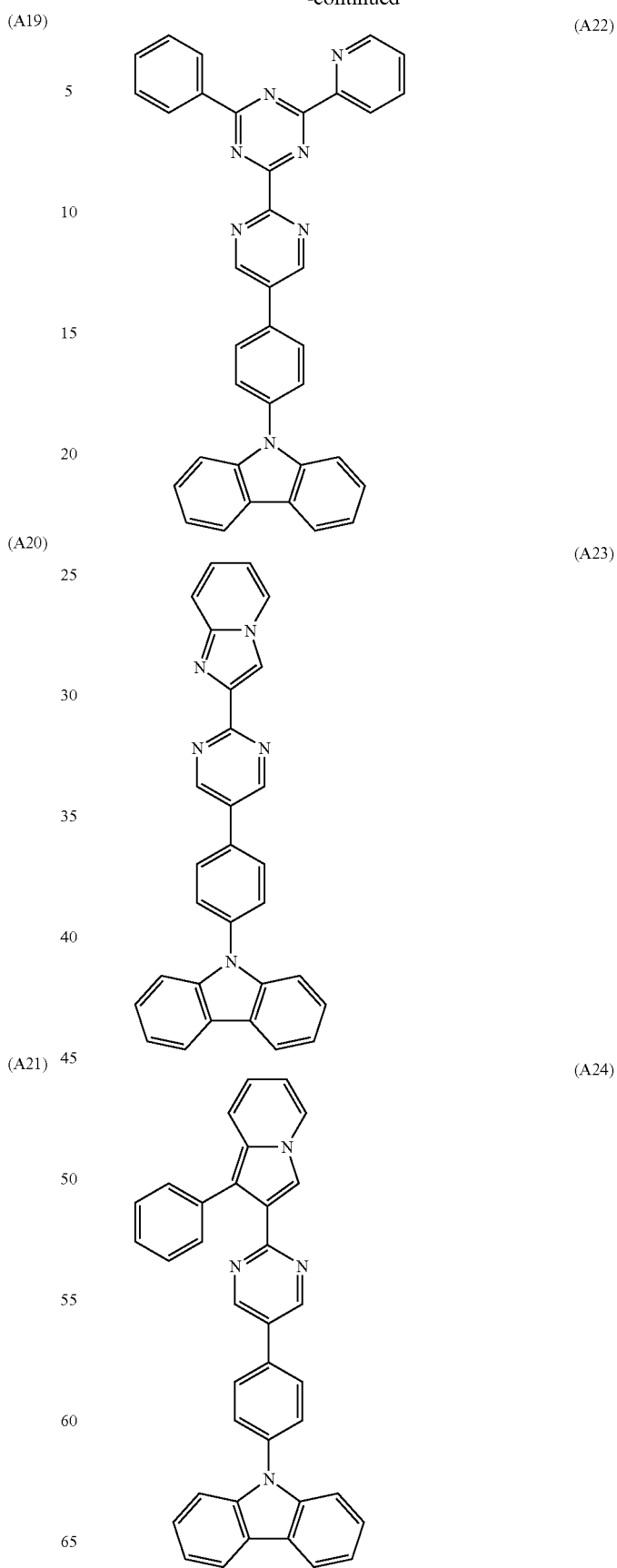

(A25) 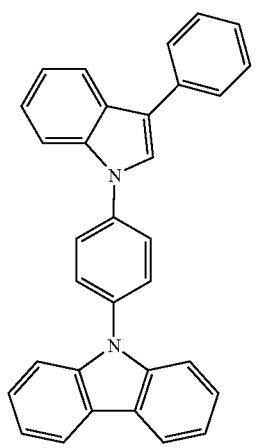
(A26) 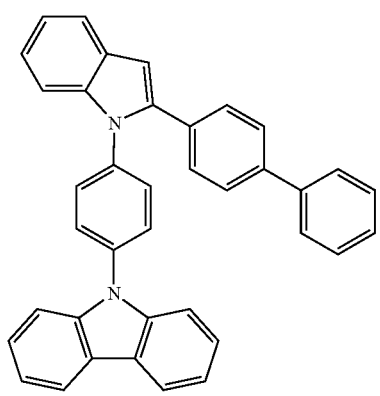
(A27) 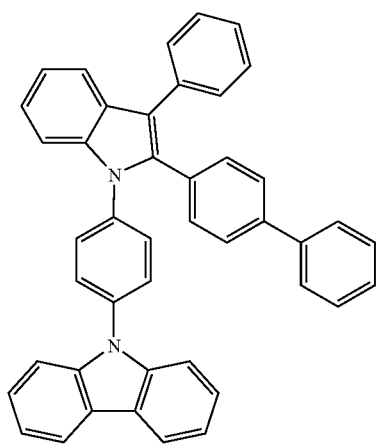
(A28) 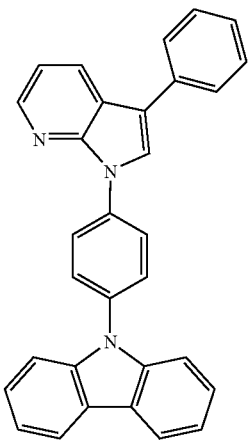
(A29) 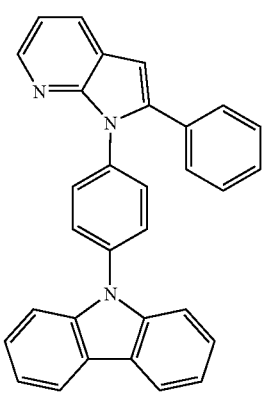
(A30) 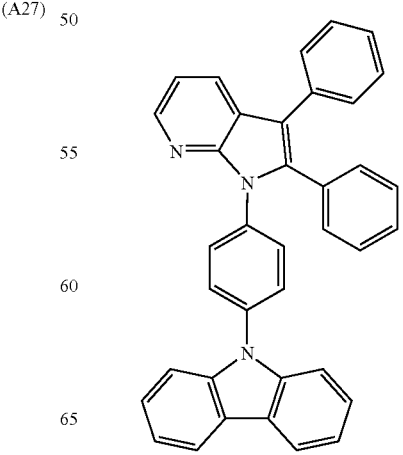

(A31)
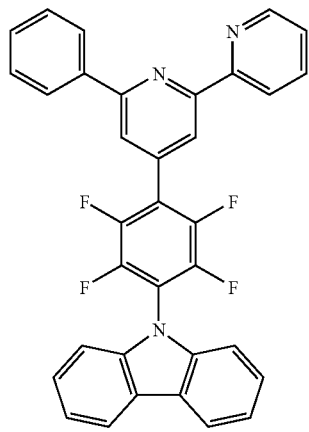
(A34)
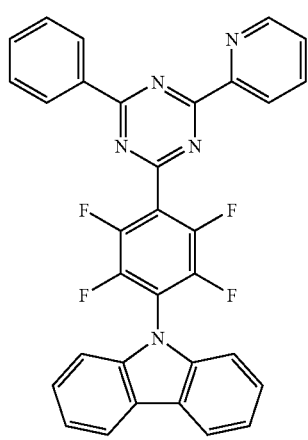
(A32)
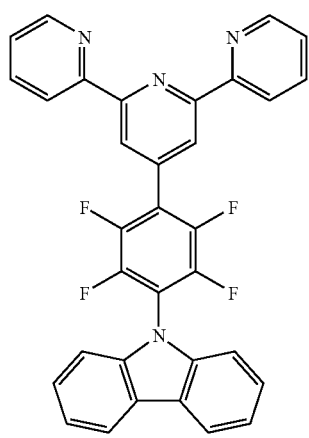
(A35)
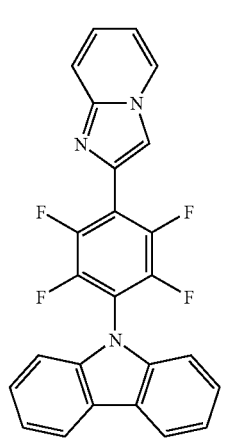
(A33)
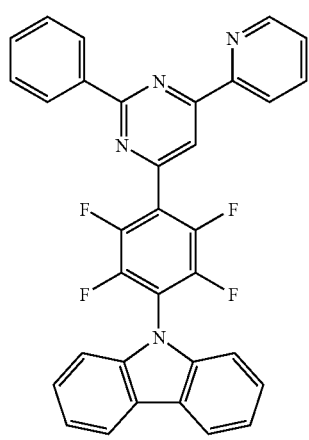
(A36)
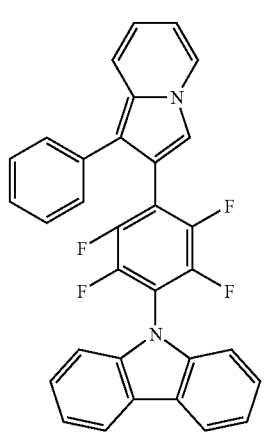

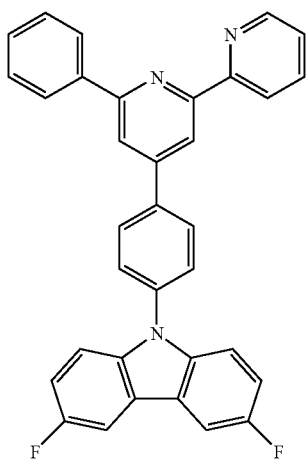 (A37)
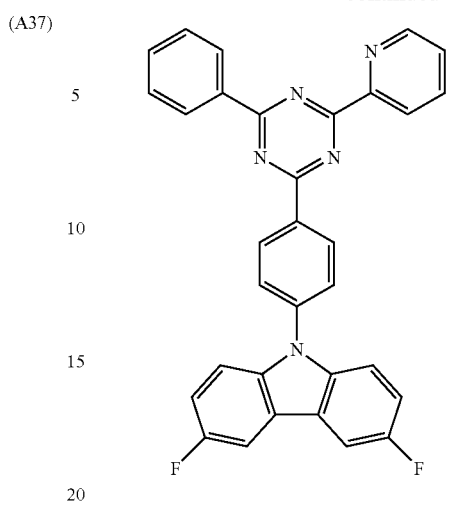 (A40)
(A38)
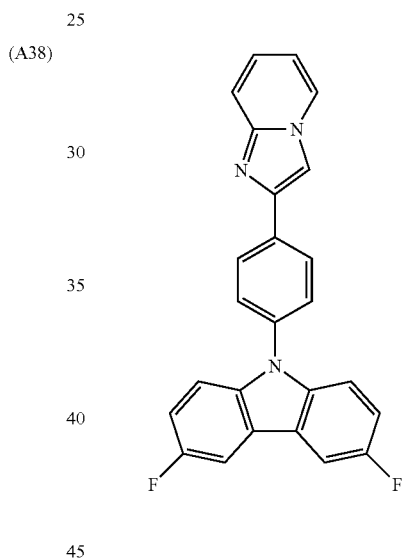 (A41)
(A39)
(A42)
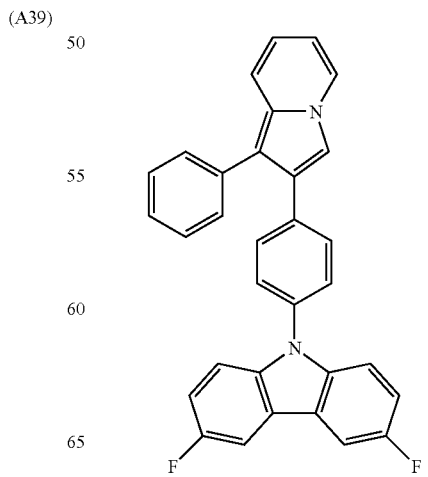

-continued
(A43)
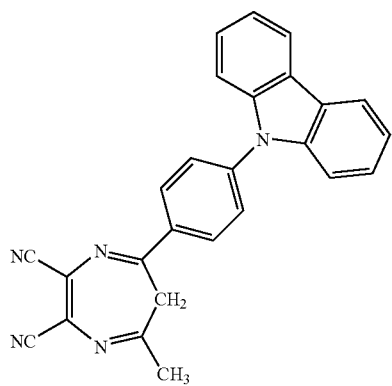
(A44)
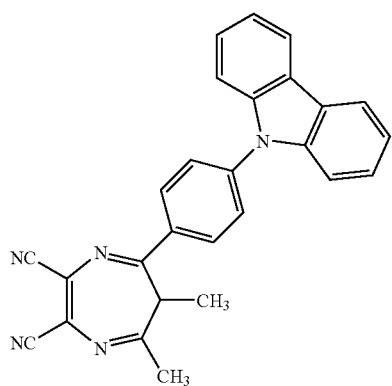
(A45)
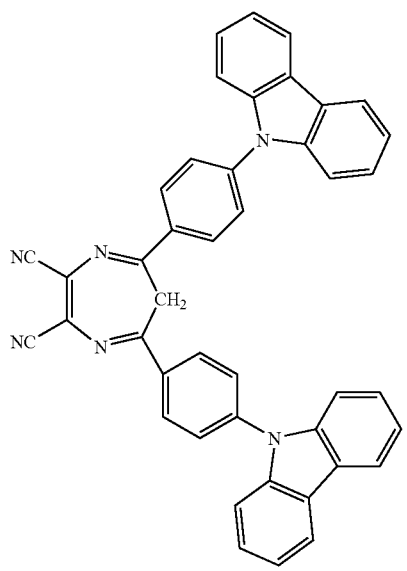
-continued
(A46)
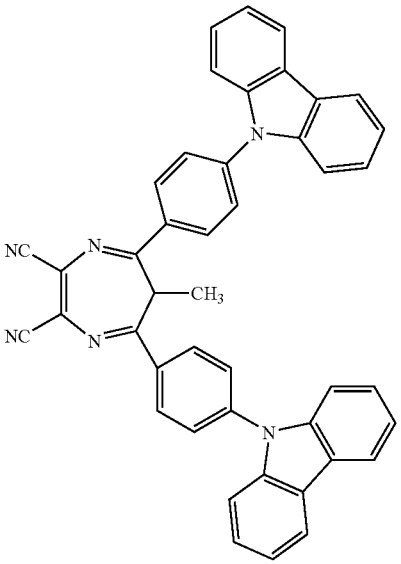
(A47)
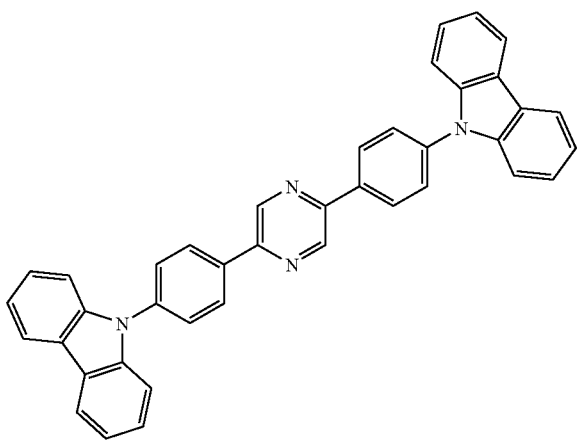
(A48)

(A49)
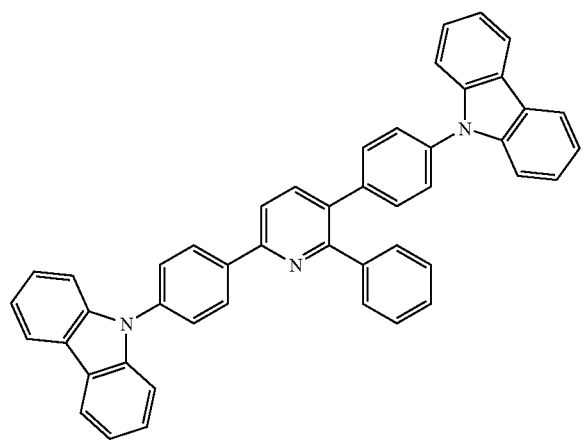
(A50)
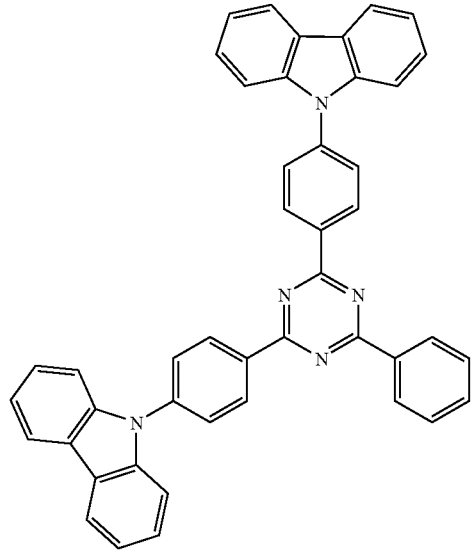
(A51)
(A52)
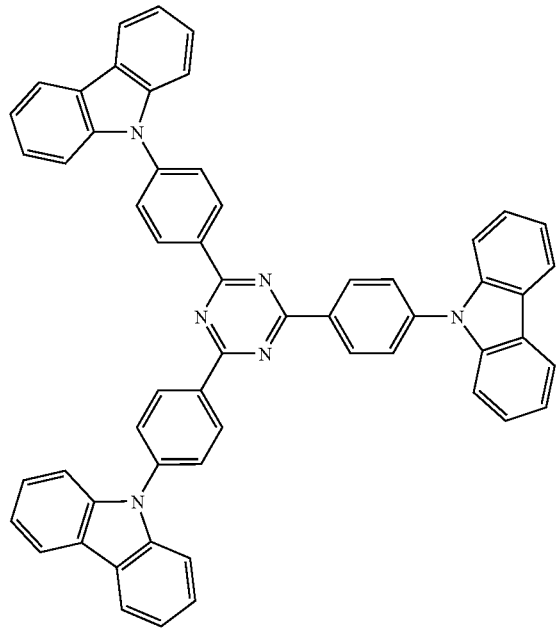
(A53)
(A54)
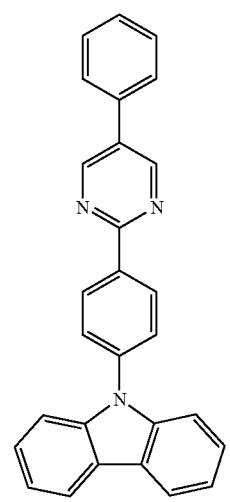

(A55) 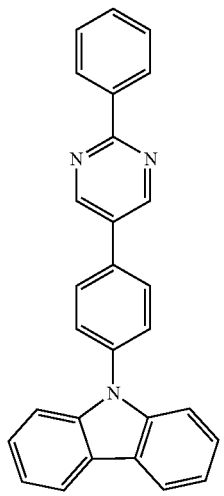
(A56) 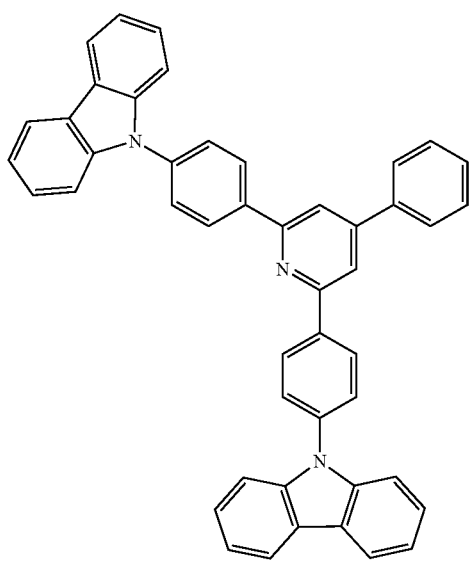
(A57) 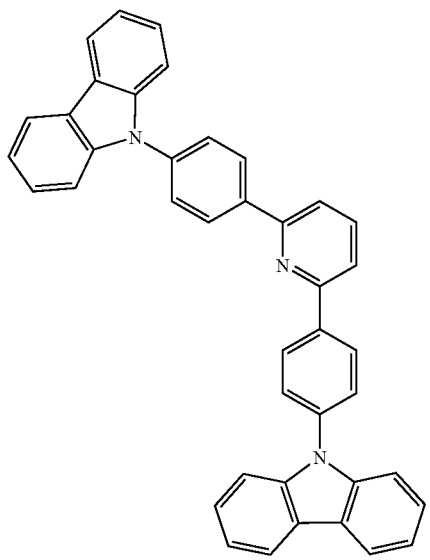
(A58) 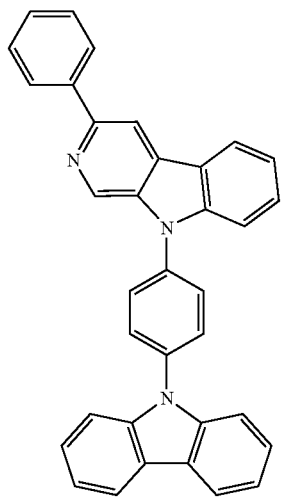
(A59) 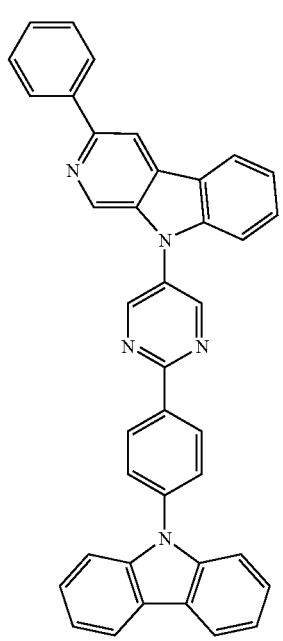
(A60) 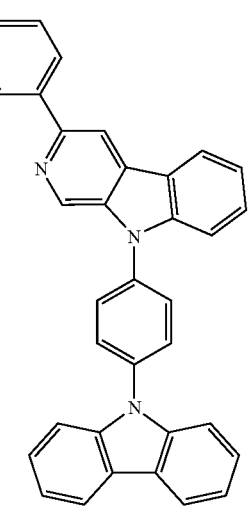

(A61)
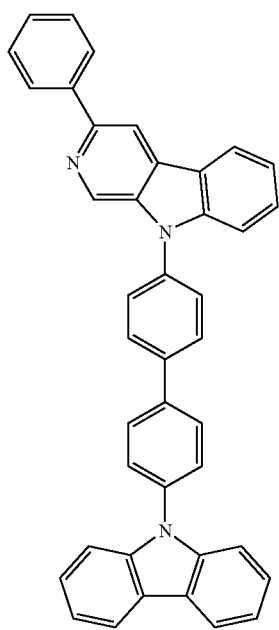
(A62)
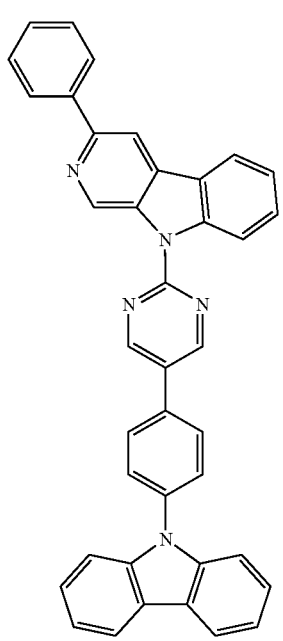
(A63)
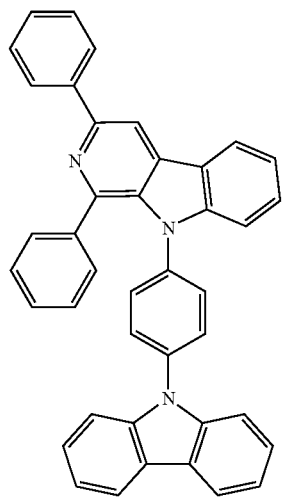
(A64)
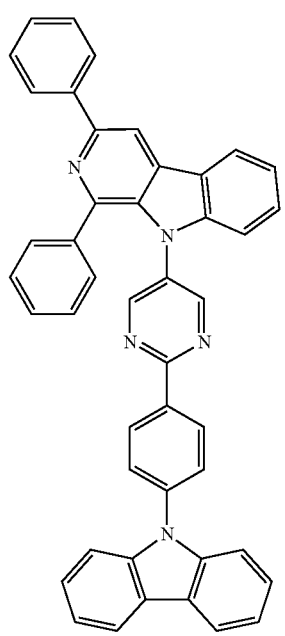
(A65)
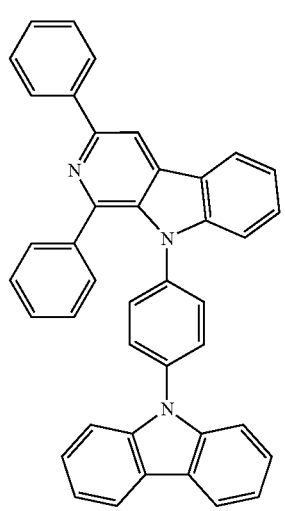

(A66)
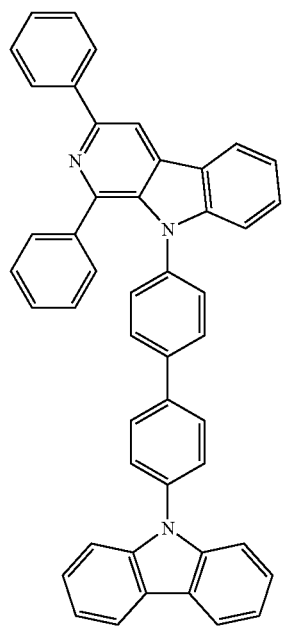
(A67)
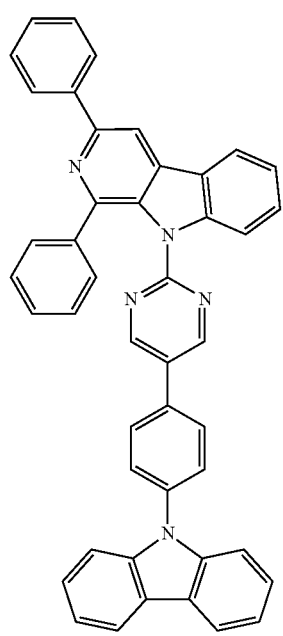
(A68)
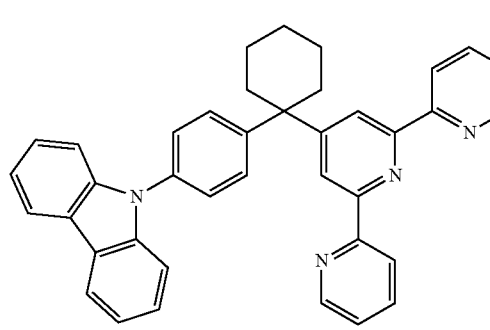
(A69)
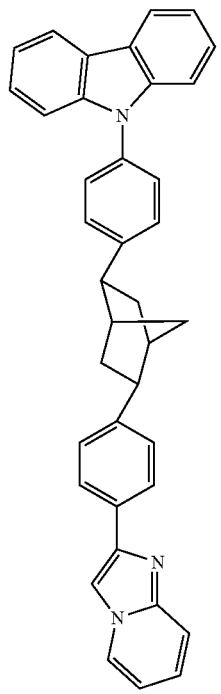
(A70)
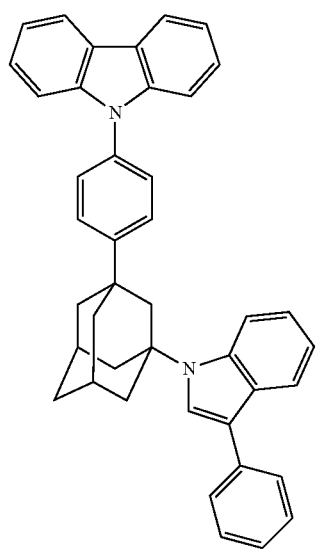

(A71)
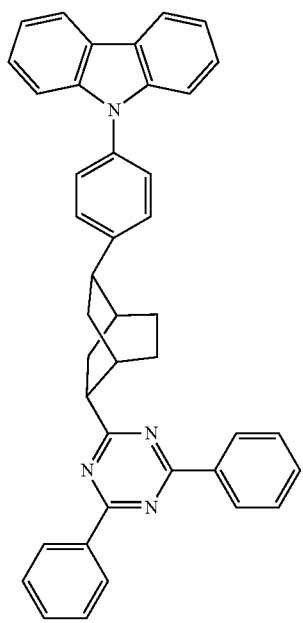
(A72)
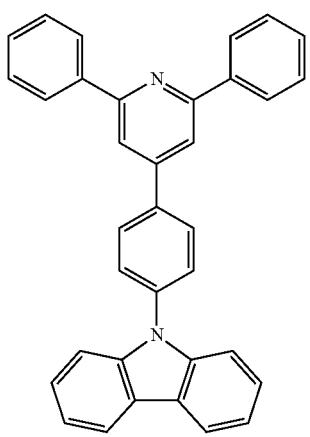
(A73)
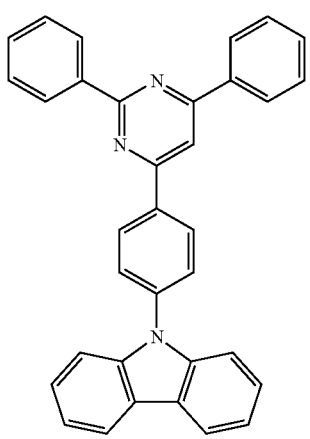
(A74)
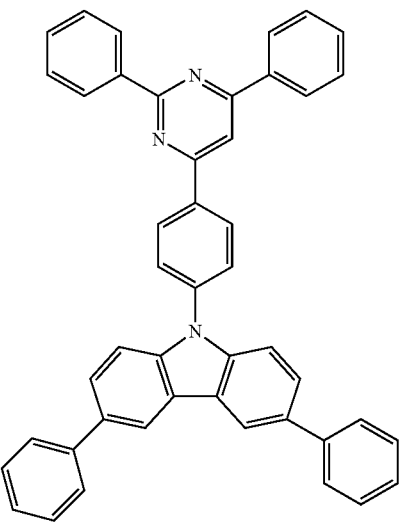
(A75)
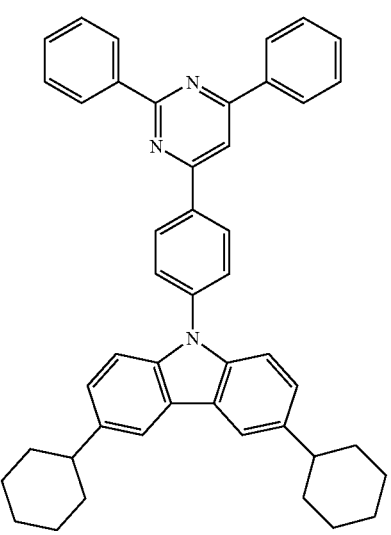
(A76)
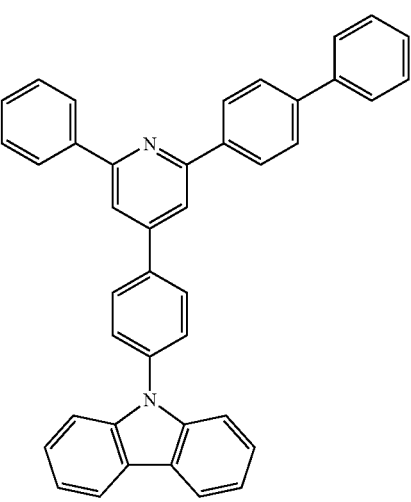

(A77)
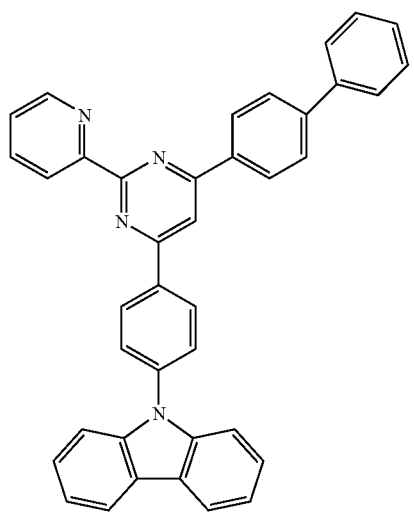
(A78)
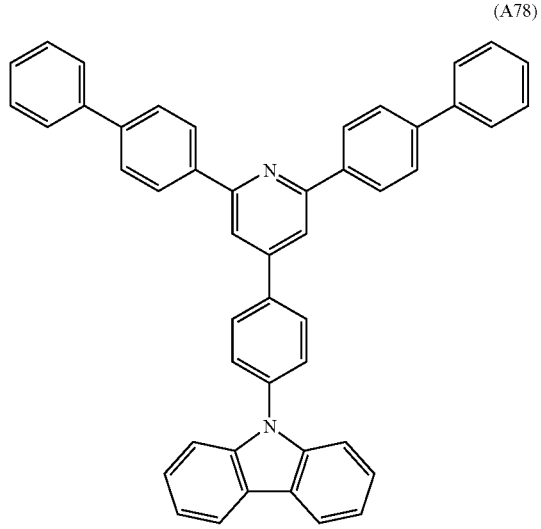
(A79)
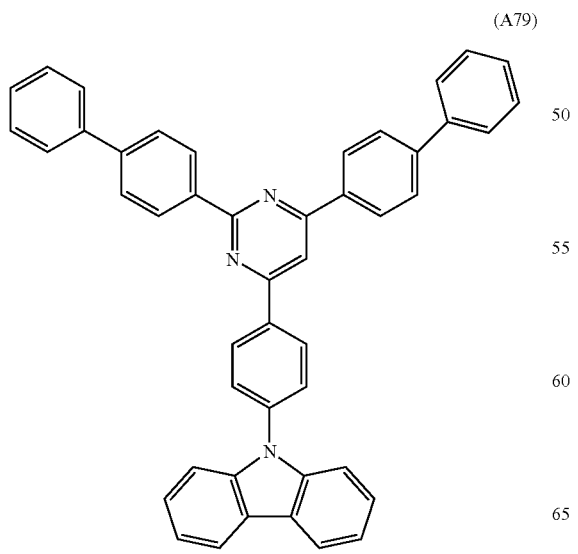
(A80)
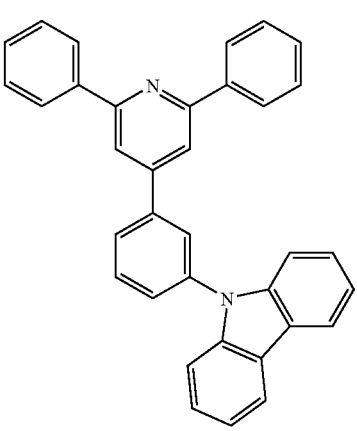
(A81)
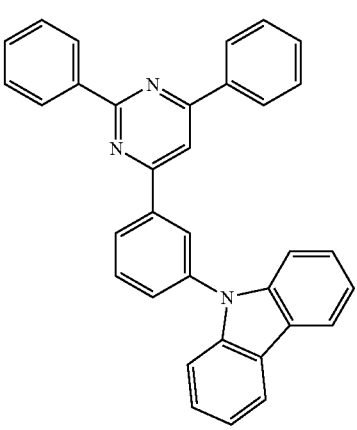
(A82)
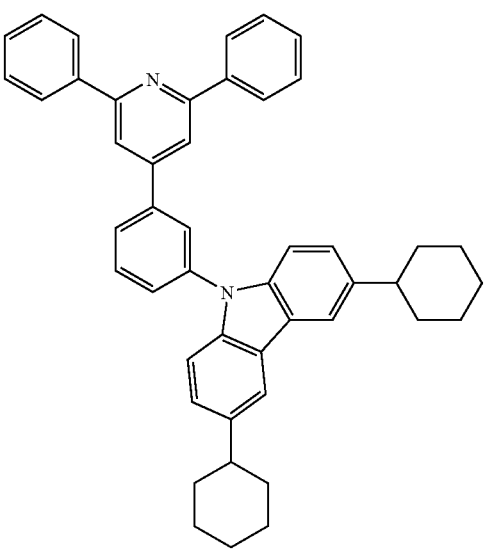

(A83)
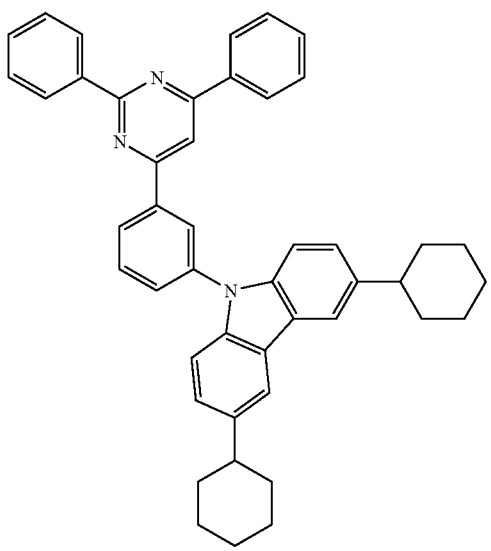
(A84)
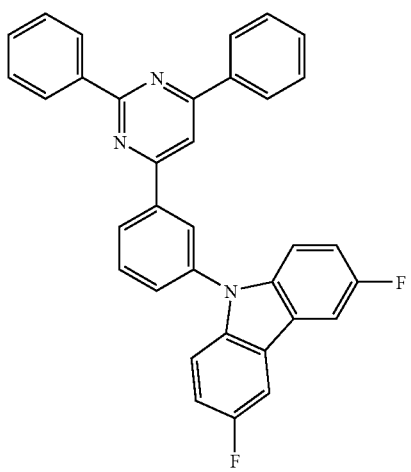
(A85)
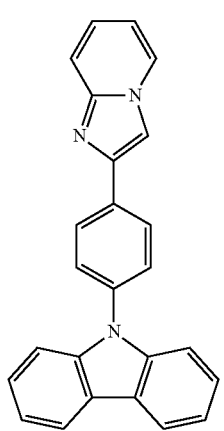
(A86)
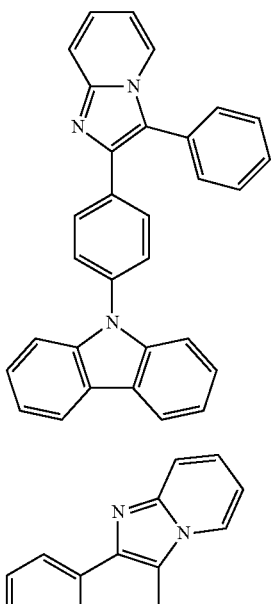
(A87)
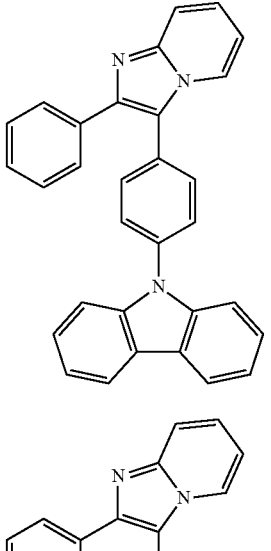
(A88)
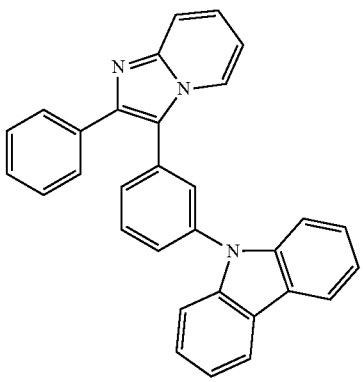
(A89)
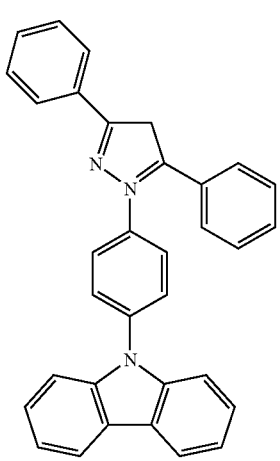

(A90)
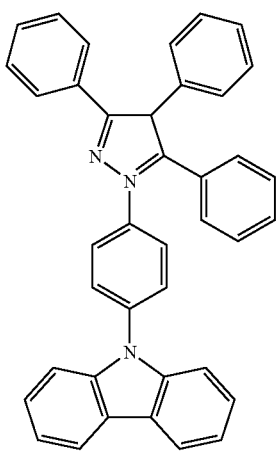
(A91)
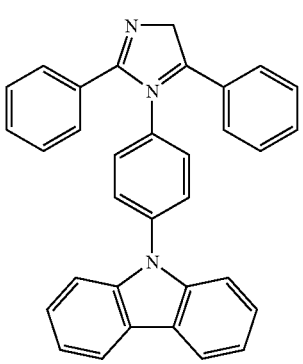
(A92)
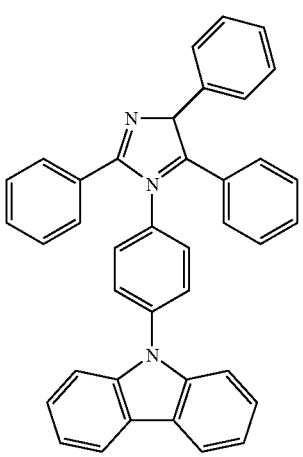
(A93)
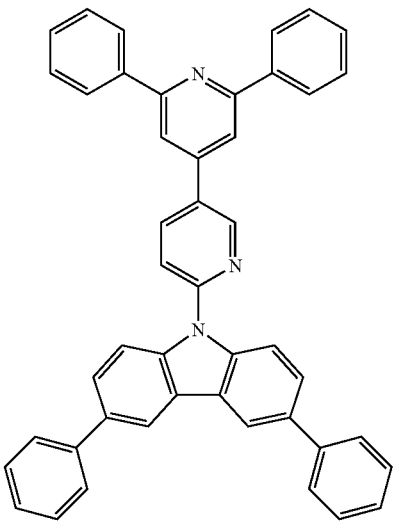
(A94)
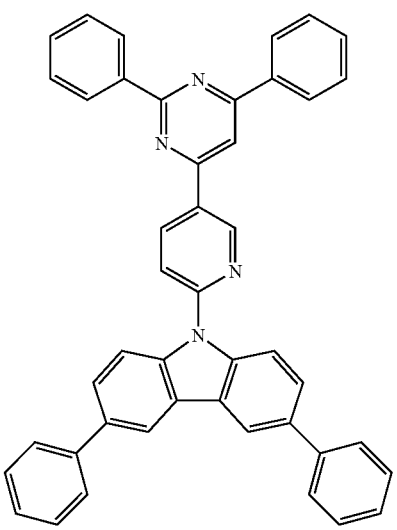
(A95)
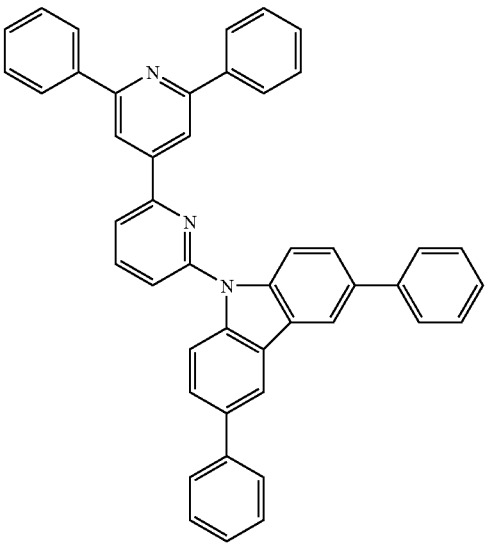

(A96)
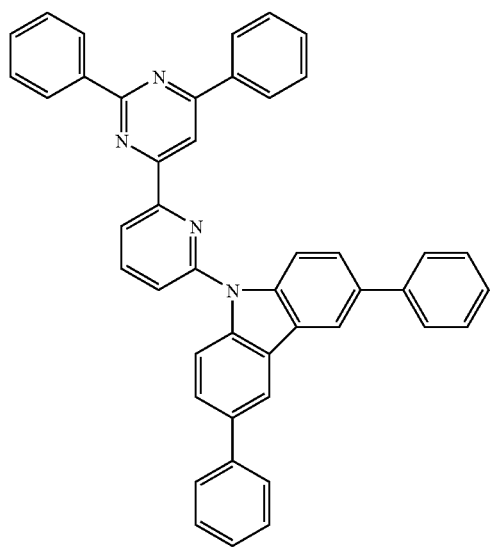
(A97)
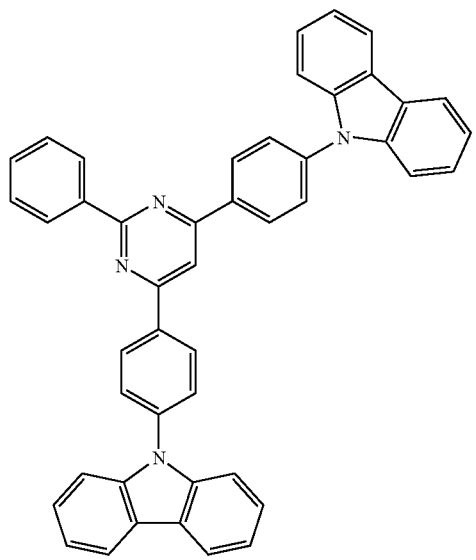
(A98)
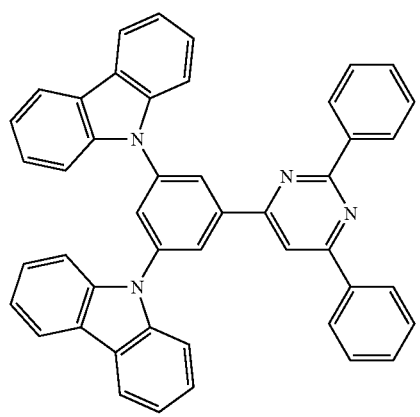
(A99)
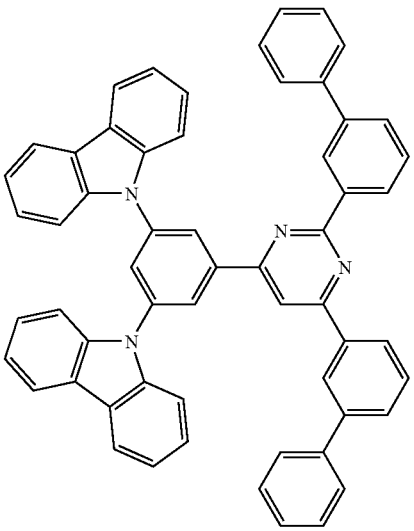
(A100)
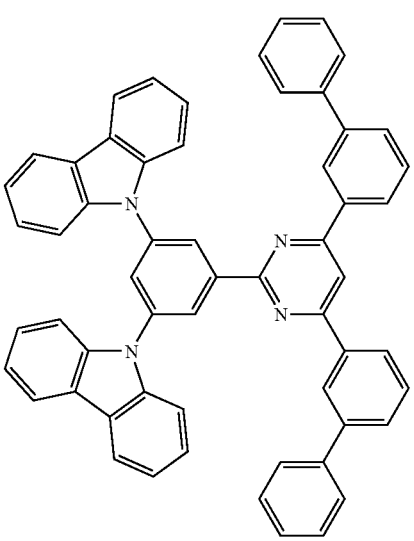
(A101)
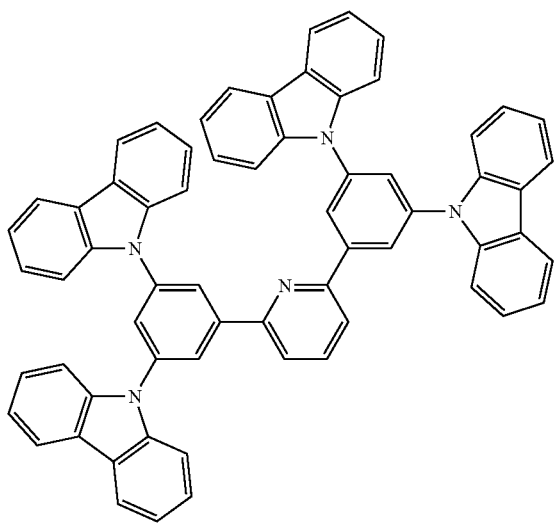

(A102)
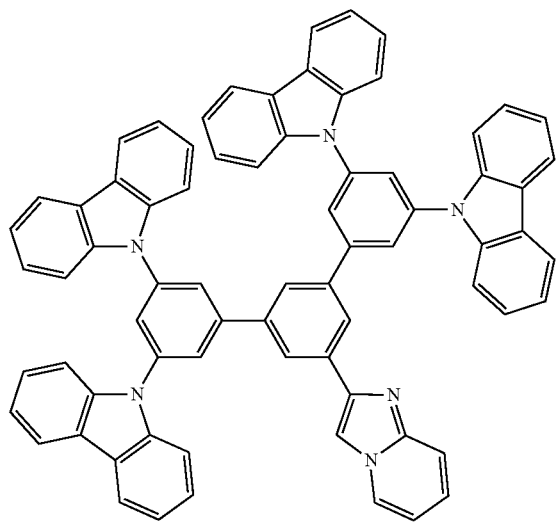
(A105)
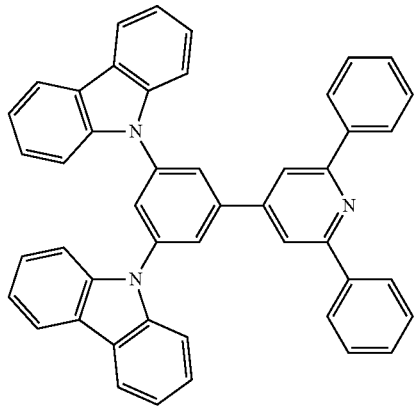
(A103)
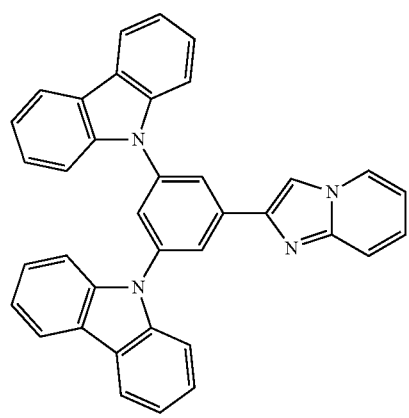
(A106)
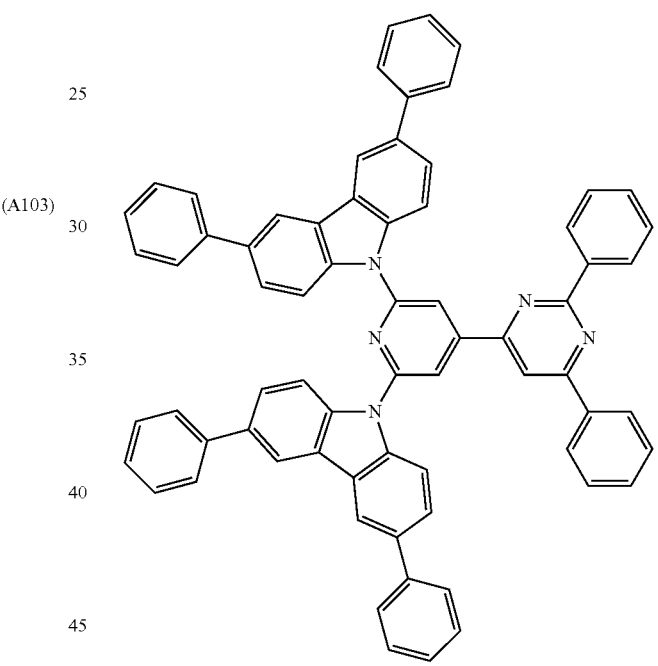
(A104)
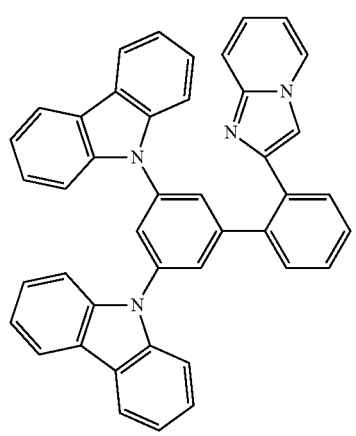
(A107)
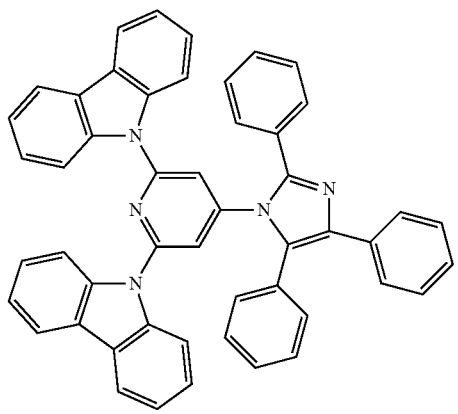

(A108)
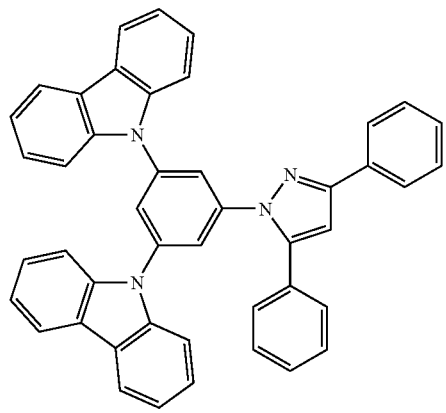
(A109)
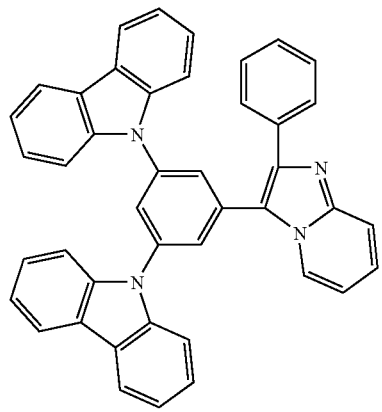
(A110)
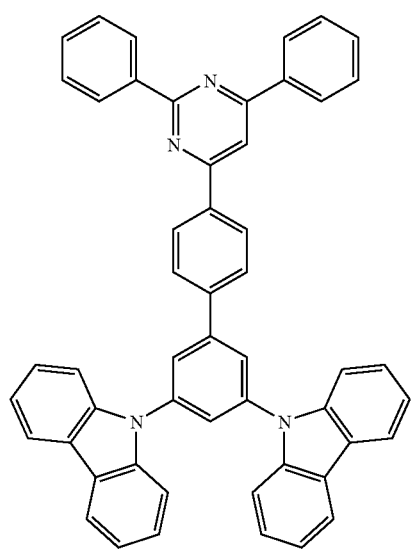
(A111)
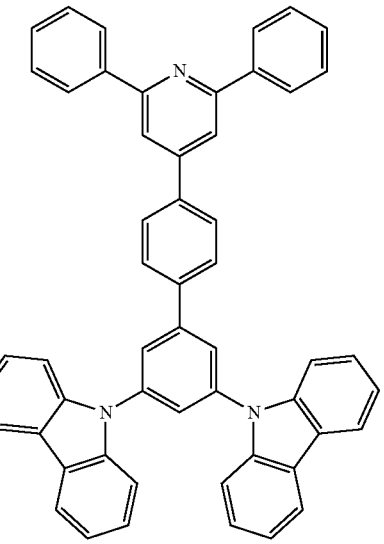
(A112)
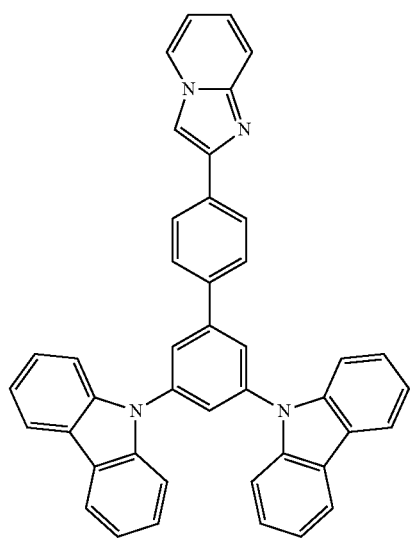
(A113)
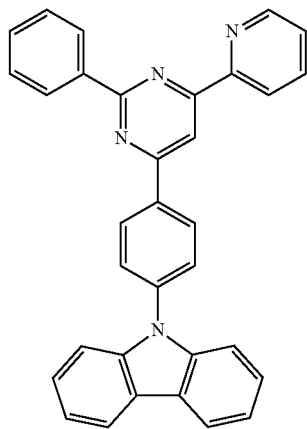

(A114)
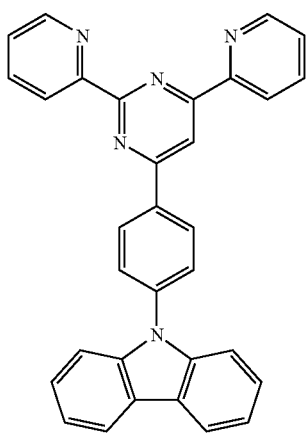
(B3)
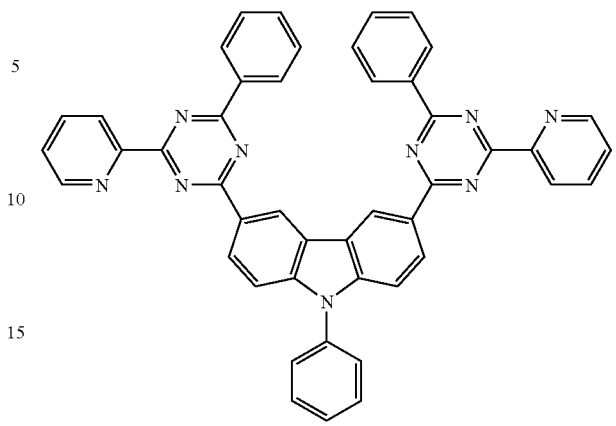
Specific examples of the compound represented by general formula (2) are shown in the following. However, the compound represented by general formula (2) is not limited to these compounds.
(B1)
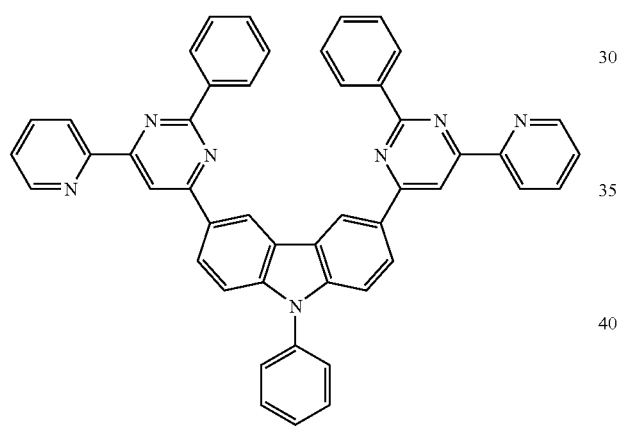
(B4)
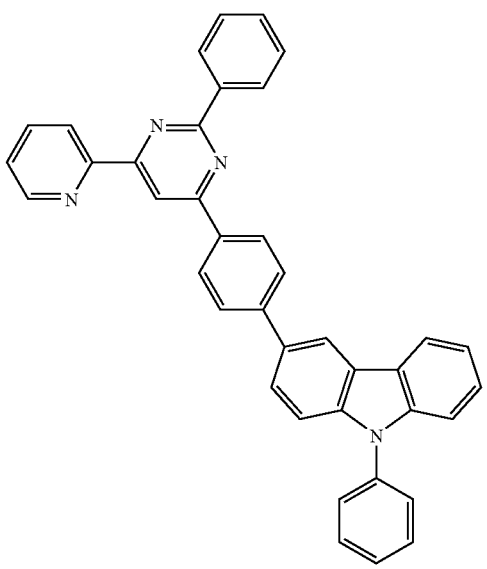
(B2)
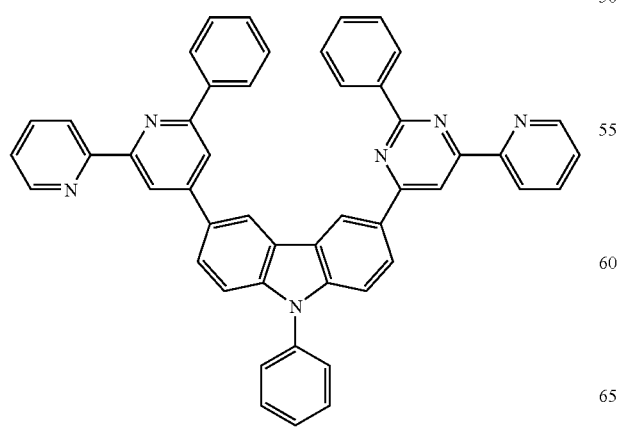
(B5)
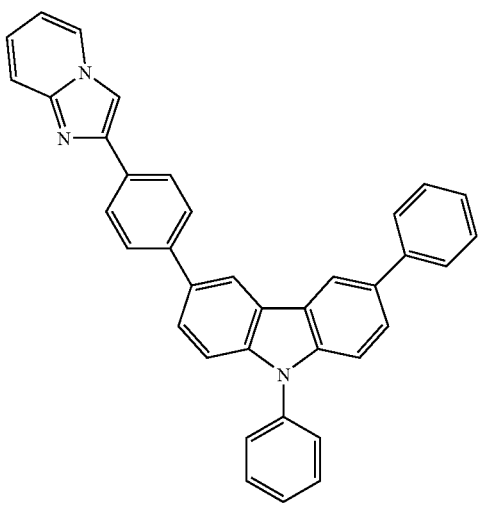

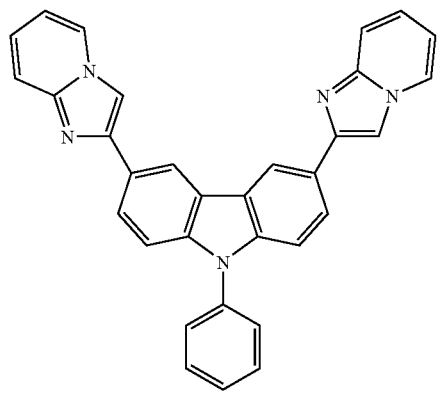
(B6)
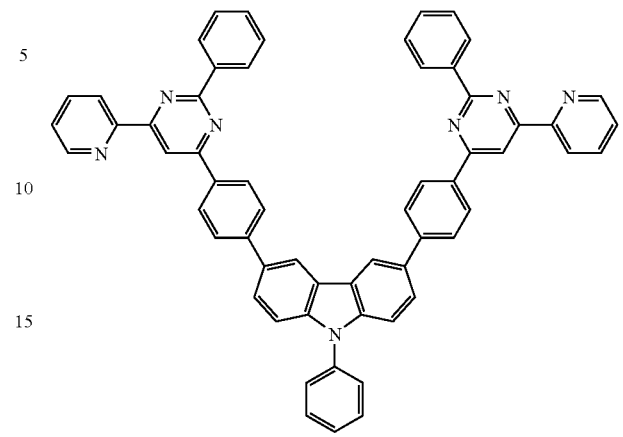
(B9)
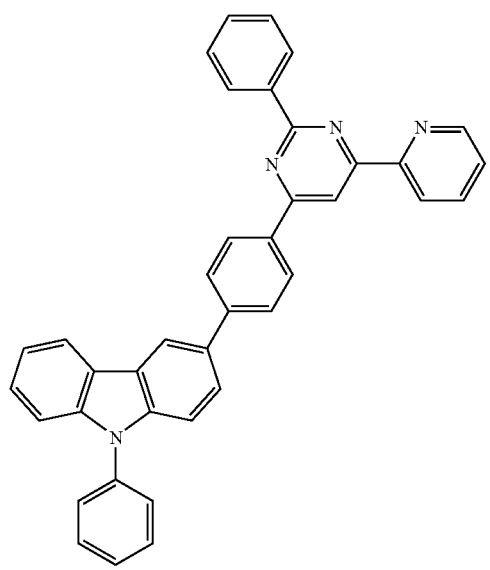
(B7)
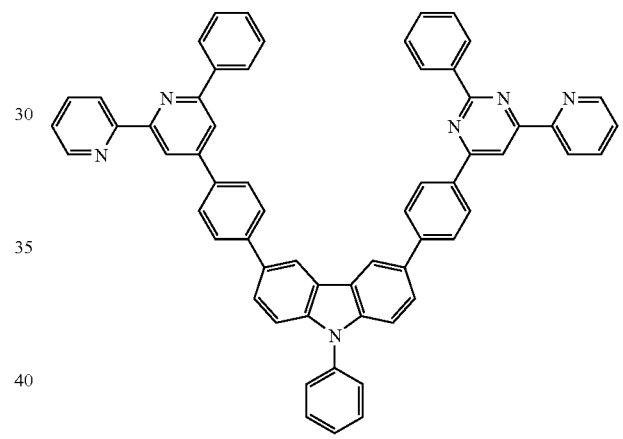
(B10)
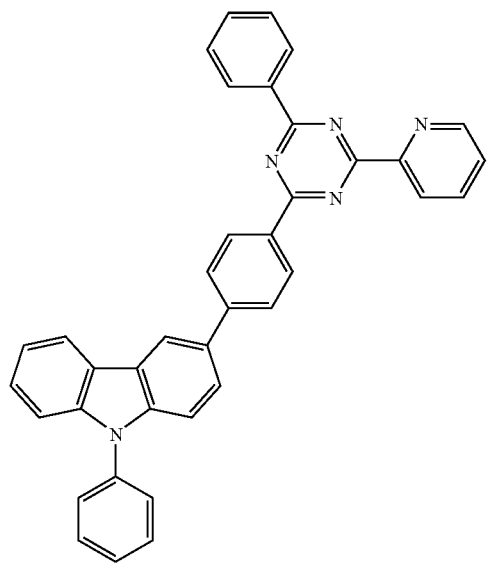
(B8)
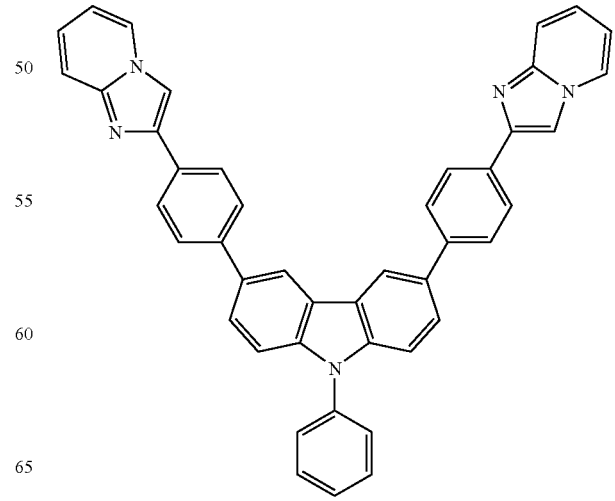
(B11)

(B12)

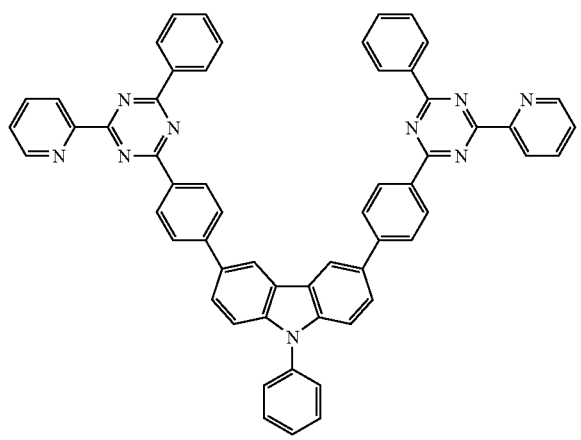

(B13)

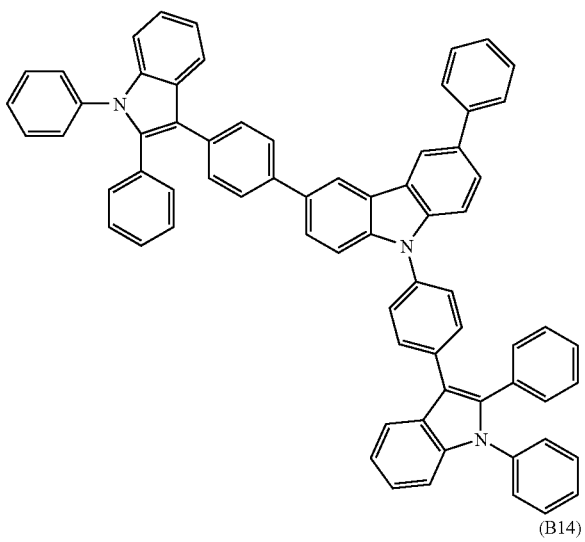

(B14)

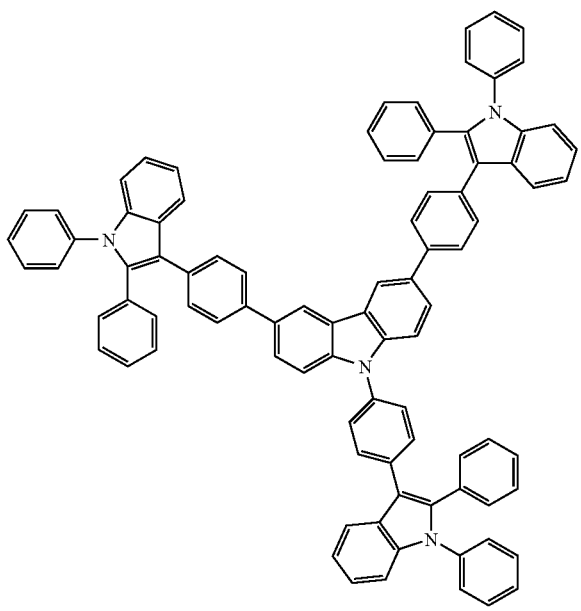

It is preferable that the energy gap of the triplet state of a compound represented by general formula (1) or (2) is 2.5 to 3.3 eV and more preferably 2.5 to 3.2 eV.

It is preferable that the energy gap of the singlet state of a compound represented by general formula (1) or (2) is 2.8 to 3.8 eV and more preferably 2.9 to 3.7 eV.

The organic EL device of the present invention comprises an anode, a cathode and an organic thin film layer comprising at least one layer disposed between the anode and the cathode, wherein at least one layer in the organic thin film layer comprises the material for organic electroluminescence devices comprising the compound represented by the above general formula (1) or (2).

It is preferable that the organic EL device of the present invention comprises the material for organic electroluminescence devices comprising the compounds represented by the above general formula (1) or (2) in the light emitting layer, the electron transporting layer or the hole transporting layer.

The organic EL device of the present invention emits bluish light and the purity of color of the emitted light is as excellent as (0.12, 0.10) to (0.17, 0.20). This property is exhibited since the material for organic EL devices comprising the compound represented by general formula (1) or (2) of the present invention has a great energy gap.

It is preferable that the organic EL device of the present invention emits light by a multiplet excitation which is the excitation to the triplet state or higher.

It is preferable that the material for organic electroluminescence devices is a host material of the organic EL device. The host material is a material into which holes and electrons can be injected and which has the function of transporting holes and electrons and emitting fluorescent light by recombination of holes and electrons.

The compounds represented by general formulae (1) and (2) in the present invention are useful also as the organic host material for phosphorescence devices since the energy gap of the singlet state is as high as 2.8 to 3.8 eV and the energy gap of the triplet state is as high as 2.5 to 3.3 eV.

The phosphorescence device is the organic device which comprises a substance emitting light based on the transition from the energy level of the triplet state to the energy level of the ground singlet state with a stronger intensity than those emitted from other substances, i.e., a phosphorescent material such as organometallic complexes comprising at least one metal selected from Groups 7 to 11 of the Periodic Table, and emits light under an electric field utilizing the so-called phosphorescence.

In the light emitting layer of the organic EL device, in general, the singlet exciton and the triplet exciton are mixed in the formed excited molecules and it is said that the ratio of the amount of the singlet exciton to the amount of the triplet exciton is 1:3 and the triplet exciton is formed in a greater amount. In conventional organic EL devices using the phosphorescence, the exciton contributing to the light emission is the singlet exciton and the triplet exciton does not emit light. Therefore, the triplet exciton is ultimately consumed as heat and the light is emitted by the singlet exciton which is formed in a smaller amount. Therefore, in these organic EL devices, the energy transferred to the triplet exciton in the energy generated by the recombination of holes and electrons causes a great loss.

In contrast, it is considered that, by using the compound of the present invention for the phosphorescence device, the efficiency of light emission three times as great as that of a device using a fluorescence can be obtained since the triplet exciton can be used for emission of light. It is also considered that, when the compound of the present invention is used for the light emitting layer of the phosphorescence device, an excited triplet state having an energy state higher than the excited triplet state of a phosphorescent organometallic complex comprising a metal selected from the Group 7 to 11 of the Periodic Table is formed; the film having a more stable form is formed; the glass transition temperature is higher (Tg: 80 to 160° C.); the holes and the electrons are efficiently transported; the compound is electrochemically and chemically stable; and the formation of impurities which may work as a trap or causes the loss in the light emission is suppressed during the preparation and the use.

The organic EL device of the present invention comprises, as described above, one or more organic thin film layers formed between the anode and the cathode. When the device comprises a single layer, a light emitting layer is formed between the anode and the cathode. The light emitting layer comprises a light emitting material and, further, a hole injecting material for transporting holes injected from the anode to the light emitting material or an electron injecting material for transporting electrons injected from the cathode to the light emitting material. It is preferable that the light emitting material exhibits a very excellent phosphorescent quantum efficiency, has a great ability of transporting both holes and electrons and forms a uniform thin layer. Examples of the organic EL device of the multi-layer type include organic EL device comprising a laminate having a multi-layer construction such as (the anode/the hole injecting layer/the light emitting layer/the cathode), (the anode/the light emitting layer/the electron injecting layer/the cathode) and (the anode/the hole injecting layer/the light emitting layer/the electron injecting layer).

For the light emitting layer, in addition to the compound represented by general formula (1) or (2) of the present invention, conventional host materials, light emitting materials, doping materials, hole injecting materials and electron injecting materials and combinations of these materials may be used, where necessary. By using a multi-layer. structure for the organic EL device, decreases in the luminance and the life due to quenching can be prevented and the luminance of emitted light and the efficiency of light emission can be improved with other doping materials. By using other doping materials contributing to the light emission of the phosphorescence in combination, the luminance of emitted light and the efficiency of light emission can be improved in comparison with conventional devices.

In the organic EL device of the present invention, the hole injecting layer, the light emitting layer and the electron injecting layer may each have a multi-layer structure. When the hole injecting layer has a multi-layer structure, the layer into which holes are injected from the electrode is called the hole injecting layer and the layer which receives holes from the hole injecting layer and transports holes to the light emitting layer is called the hole transporting layer. Similarly, when the electron injecting layer has a multi-layer structure, the layer into which electron are injected from the electrode is called the electron injecting layer and the layer which receives electrons from the electron injecting layer and transports electrons to the light emitting layer is called the electron transporting layer. The layers are selected in accordance with the energy levels of the material, heat resistance and adhesion with the organic thin film layers or the metal electrodes.

In the organic EL device of the present invention, the electron transporting layer and/or the hole transporting layer may comprise the material for organic EL devices of the present invention which comprises any of the compounds represented by general formulae (1) and (2). The hole injecting layer, the electron injecting layer and the hole barrier layer may comprise the material for organic EL devices of the present invention. A phosphorescent light emitting compound and the material for organic EL materials of the present invention may be used as a mixture.

Examples of the light emitting material and the host material which can be used for the organic thin film layer in combination with the compound represented by general formula (1) or (2) include anthracene, naphthalene, phenanthrene, pyrene, tetracene, coronen, chrysene, fluoresceine, perylene, phthaloperylene, naphthaloperylene, perynone, phthaloperynone, naphthaloperynone, diphenylbutadiene, tetraphenyl-butadiene, coumarine, oxadiazole, aldazine, bisbenzoxazoline, bisstyryl, pyrazine, cyclopentadiene, metal complexes of quinoline, metal complexes of aminoquinoline, metal complexes of benzoquinoline, imines, diphenylethylene, vinylanthracene, diaminoanthracene, diaminocarbazole, pyrane, thiopyrane, polymethine, melocyanine, oxinoid compounds chelated with imidazole, quinacridone, rubrene, stilbene-based derivatives and phosphorescent pigments. However, the light emitting material and the host material are not limited to the compounds described above.

As the light emitting material, phosphorescent organometallic complexes are preferable since the external quantum efficiency of the device can be improved. Examples of the metal in the phosphorescent organometallic complex include ruthenium, rhodium, palladium, silver, rhenium, osmium, iridium, platinum and gold. It is preferable that the organometallic complex is an organometallic compound represented by the following general formula (3):

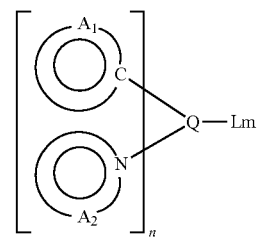

(3)

In the above general formula, $A^1$ represents a substituted or unsubstituted aromatic hydrocarbon cyclic group or aromatic heterocyclic group which is preferably phenyl group, biphenyl group, naphthyl group, anthryl group, thienyl group, pyridyl group, quinolyl group or isoquinolyl group. Examples of the substituent include halogen atoms such as fluorine atom; alkyl groups having 1 to 30 carbon atoms such as methyl group and ethyl group; alkenyl groups such as vinyl group; alkoxycarbonyl groups having 1 to 30 carbon atoms such as methoxycarbonyl group and ethoxycarbonyl group; alkoxyl groups having 1 to 30 carbon atoms such as methoxy group and ethoxyl group; aryloxy groups such as phenoxyl group and benzyloxyl group; dialkylamino groups such as dimethylamino group and diethylamino group; acyl groups such as acetyl group; haloalkyl groups such as trifluoromethyl group; and cyano group.

$A^2$ represents a substituted or unsubstituted aromatic heterocyclic group having nitrogen atom as the atom forming the heterocyclic ring, which is preferably pyridyl group, pirimidyl group, pyrazine group, triazine group, benzothiazole group, benzoxazole group, benzimidazole group, quinolyl group, isoquinolyl group, quinoxaline group or phenanthridine group. Examples of the substituent include the substituents described as the examples of the substituent for the group represented by $A^1$.

The ring having the group represented by $A^1$ and the ring having the group represented by $A^2$ may form one condensed ring. Examples of the condensed ring include 7,8-benzo-quinoline group.

Q represents a metal selected from metals of Groups 7 to 11 of the Periodic Table, which is preferably ruthenium, rhodium, palladium, silver, rhenium, osmium, iridium, platinum or gold.

L represents a bidentate ligand, which is preferably selected from ligands of the β-diketone type such as acetylacetonates and pyromellitic acid.

m and n each represent an integer. When Q represents a divalent metal, n=2 and m=0. When Q represents a trivalent metal, n=3 and m=0 or n=2 and m=1.

Specific examples of the organometallic complex represented by the above general formula (3) are shown in the following. However, the organometallic complex is not limited to these compounds.

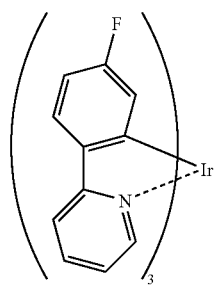
(K-1)

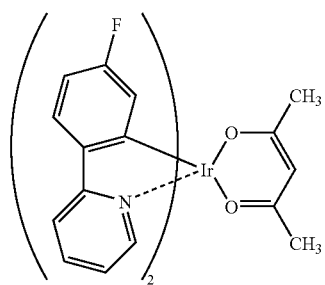
(K-2)

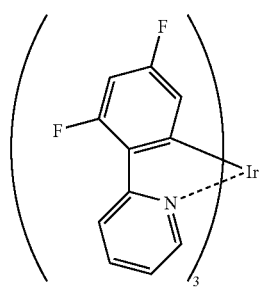
(K-3)

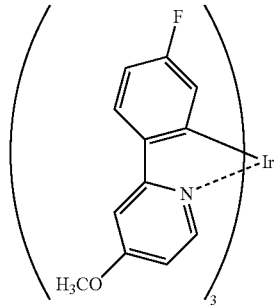
(K-4)

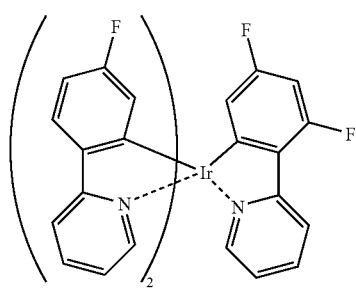
(K-5)

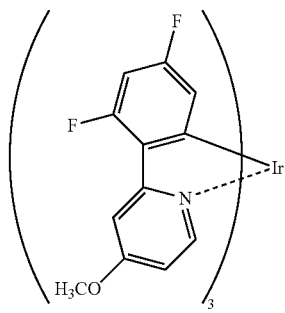
(K-6)

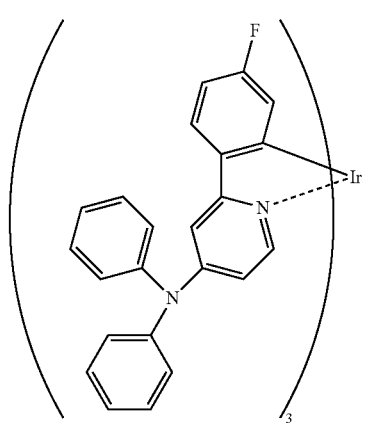
(K-7)

(K-8)
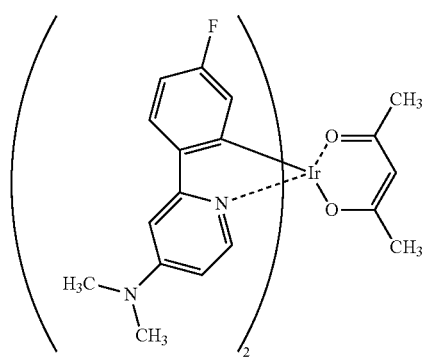
(K-9)
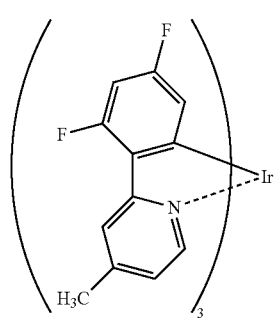
(K-10)
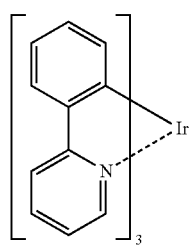
(K-11)
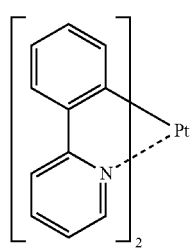
(K-12)
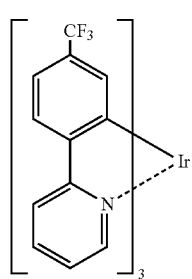
(K-13)
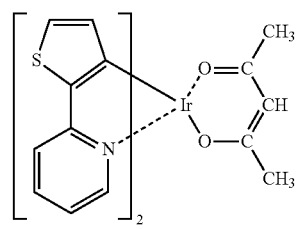
(K-14)
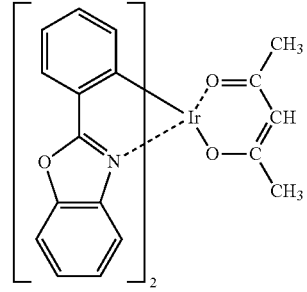
(K-15)
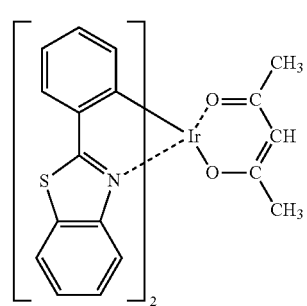
(K-16)
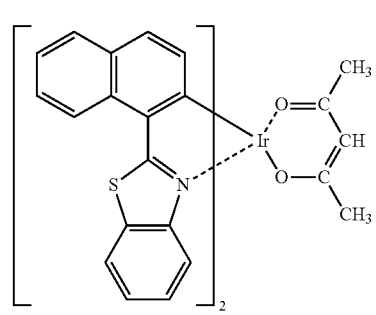
(K-17)
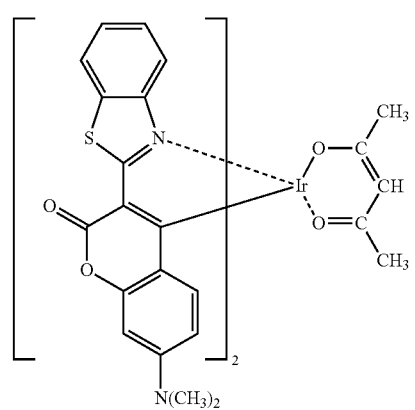

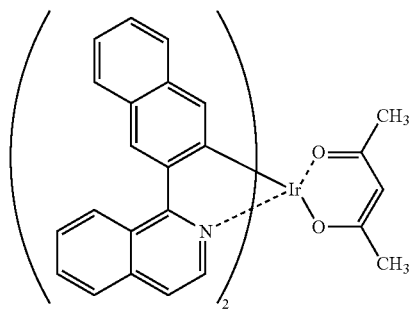

(K-18)

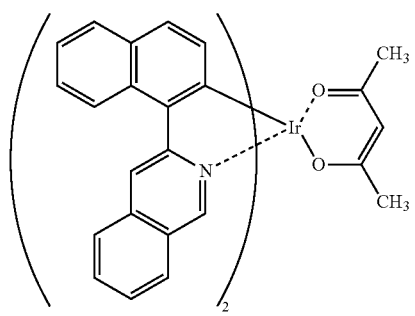

(K-19)

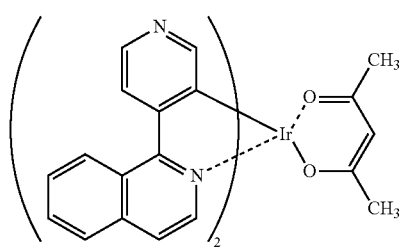

(K-20)

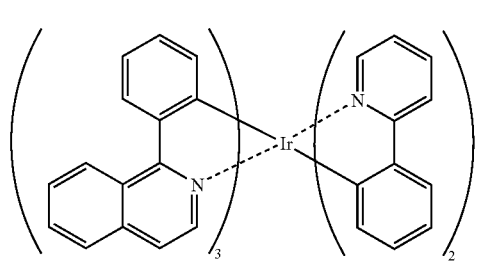

(K-21)

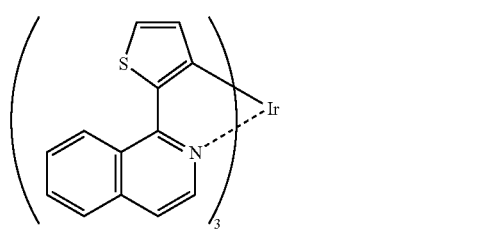

(K-22)

As the hole injecting material, compounds which have the ability to transport holes, exhibits the excellent effect of receiving holes injected from the anode and the excellent effect of injecting holes to the light emitting layer or the light emitting material, prevents transfer of excitons formed in the light emitting layer to the electron injecting layer or the electron injecting material and has the excellent ability of forming a thin film, are preferable. Examples of the hole injecting compound include phthalocyanine derivatives, naphthalocyanine derivatives, porphyrin derivatives, oxazoles, oxadiazoles, triazoles, imidazoles, imidazolones, imidazolethiones, pyrazolines, pyrazolones, tetrahydroimidazoles, hydrazones, acylhydrazones, polyarylalkanes, stilbene, butadiene, triphenylamine of the benzidine type, triphenylamine of the styrylamine type, triphenylamine of the diamine type, derivatives of the above compounds and macromolecular materials such as polyvinyl-carbazoles, polysilanes and electrically conductive macromolecules. However, the hole injecting material is not limited to these materials.

Among these hole injecting materials, the more effective hole injecting materials are aromatic tertiary amine derivatives and phthalocyanine derivatives. Examples of the aromatic tertiary amine derivative include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane and oligomers and polymers having the skeleton structure of these aromatic tertiary amines. However, the aromatic tertiary amine is not limited to these compounds. Examples of the phthalocyanine (Pc) derivative include phthalocyanine derivatives and naphthalocyanine derivatives such as $H_2Pc$, CuPc, CoPc, NiPc, ZnPc, PdPc, FePc, MnPc, ClAlPC, ClGaPc, ClInPc, ClSnPc, $Cl_2SiPc$, (HO)AlPc, (HO)GaPc, VOPc, TiOPc, MoOPc and GaPc—O—GaPc. However the phthalocyanine derivative is not limited to these compounds.

As the electron injecting material, compounds which have the ability to transport electrons, exhibits the excellent effect of receiving electrons injected from the anode and the excellent effect of injecting electrons to the light emitting layer or the light emitting material, prevents transfer of excitons formed in the light emitting layer to the hole injecting layer and has the excellent ability of forming a thin film, are preferable. Examples of the electron injecting compound include fluorenone, anthraquinodimethane, diphenoquinone, thiopyrane dioxide, oxazoles, oxadiazoles, triazoles, imidazoles, perylenetetracarboxylic acid, quinoxaline, fluorenylidenemethane, anthraquinodimethane, anthrone and derivatives of these compounds. However, the electron injecting material is not limited to these compounds.

Among these electron injecting materials, the more effective electron injecting materials are metal complex compounds and five-membered derivatives having nitrogen. Examples of the metal complex compound include 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum and bis(2-methyl-8-quinolinato)(2-naphtholato)gallium. However the electron injecting material is not limited to these compounds.

As the five-membered derivative having nitrogen, oxazoles, thiazoles, oxadiazoles, thiadiazoles, triazoles and derivatives of these compounds are preferable. Examples of the five-membered derivative having nitrogen include bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,5-oxadiazole, 2,5-bis(1-naphthyl)-1,3,4-oxadiazole, 1,4-bis[2-(5- phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole and 1,4-bis [2-(5-phenyltriazolyl)]benzene. However, the five-membered derivative having nitrogen is not limited to these compounds.

The property of charge injection can be improved by adding an electron-accepting compound to the hole injecting material and an electron-donating compound to the electron injecting material.

As the electrically conductive material used for the anode of the organic EL device of the present invention, a material having a work function greater than 4 eV is suitable and carbon, aluminum, vanadium, iron, cobalt, nickel, tungsten, silver, gold, platinum, palladium, alloys of these metals, metal oxides such as tin oxides and indium oxide used for ITO substrates and NESA substrates and organic electrically conductive resins such as polythiophene and polypyrrol are used. As the electrically conductive material used for the cathode, a material having a work function smaller than 4 eV is suitable and magnesium, calcium, tin, lead, titanium, yttrium, lithium, ruthenium, manganese, aluminum and alloys of these metals are used. However, the electrically conductive material used for the cathode is not limited to these materials. Typical examples of the alloy include magnesium/silver, magnesium/indium and lithium/aluminum. However, the alloy is not limited to these alloys. The composition of the alloy is controlled by the temperature of the source of vaporization, the atmosphere and the degree of vacuum and a suitable composition is selected. The anode and the cathode may be formed with a structure having two or more layers, where necessary.

The organic EL device of the present invention may comprise an inorganic compound layer between at least one of the electrodes and the above organic thin film layer. Examples of the inorganic compound used for the inorganic compound layer include various types of oxides, nitrides and oxide nitrides such as alkali metal oxides, alkaline earth metal oxides, rare earth oxides, alkali metal halides, alkaline earth metal halides, rare earth halides, $SiO_x$, $AlO_x$, $SiN_x$, SiON, AlON, $GeO_x$, $LiO_x$, LiON, $TiO_x$, TiON, $TaO_x$, TaON, $TaN_x$ and C. In particular, as the component contacting the anode, $SiO_x$, $AlO_x$, $SiN_x$, SiON, AlON, $GeO_x$ and C are preferable since a stable interface layer of injection is formed. As the component contacting the cathode, LiF, $MgF_2$, $CaF_2$ and NaF are preferable.

In the organic EL device of the present invention, it is preferable that at least one face is sufficiently transparent in the region of the wavelength of the light emitted by the device so that the light emission is achieved efficiently. It is preferable that the substrate is also transparent.

For the transparent electrode, the conditions in the vapor deposition or the sputtering are set so that the prescribed transparency is surely obtained using the above electrically conductive material. It is preferable that the electrode of the light emitting face has a transmittance of light of 10% or greater. The substrate is not particularly limited as long as the substrate has the mechanical and thermal strength and is transparent. Examples of the substrate include glass substrates and transparent films of resins. Examples of the transparent film of a resin include films of polyethylene, ethylene-vinyl acetate copolymers, ethylene-vinyl alcohol copolymers, polystyrene, polymethyl methacrylate, polyvinyl chloride, polyvinyl alcohol, polyvinyl butyral, nylon, polyether ether ketones, polysulfones, polyether sulfones, tetrafluoroethylene-perfluoroalkyl vinyl ether copolymers, polyvinyl fluoride, tetrafluoro-ethylene-ethylene copolymers, tetrafluoroethylene-hexafluoropropylene copolymers, polychlorotrifluoroethylene, polyvinylidene fluoride, polyesters, polycarbonates, polyurethanes, polyether imides, polyimides and polypropylene.

In the organic EL device of the present invention, it is possible that a protective layer is formed on the surface of the device or the entire device is covered with a silicone oil or a resin so that stability to the temperature, the humidity and the atmosphere is improved.

For the formation of each layer of the organic EL device of the present invention, any of the dry processes of film formation such as the vacuum vapor deposition, the sputtering, the plasma plating and the ion plating and the wet processes of film formation such as the spin coating, the dipping and the flow coating, can be applied. The thickness of each film is not particularly limited. However, it is necessary that the thickness of the film be set at a suitable value. When the thickness is excessively great, application of a greater voltage is necessary to obtain the same output of the light and the efficiency of light emission decreases. When the thickness is excessively small, pin holes are formed and sufficient light emission cannot be obtained even when an electric field is applied. In general, a thickness in the range of 5 nm to 10 µm is suitable and a thickness in the range of 10 nm to 0.2 µm is preferable.

When the wet process of film formation is used, the material forming each layer is dissolved or suspended in a suitable solvent such as ethanol, chloroform, tetrahydrofuran and dioxane and a thin film is formed from the obtained solution or suspension. Any of the above solvents can be used. For any of the layers, suitable resins, and additives may be used to improve the property for film formation and to prevent formation of pin holes in the film. Examples of the resin which can be used include insulating resins such as polystyrene, polycarbonates, polyarylates, polyesters, polyamides, polyurethanes, polysulfones, polymethyl methacrylate, polymethyl acrylate, cellulose and copolymers of these resins; photoconductive resins such as poly-N-vinylcarbazole and polysilanes; and electrically conductive resins such as polythiophene and polypyrrol. Examples of the additive include antioxidants, ultraviolet light absorbents and plasticizers.

As described above, by using the compound represented by general formula (1) or (2) for the organic thin film layer of the organic EL device of the present invention, the organic EL device emitting blue light with a high purity of color can be obtained. This organic EL device can be advantageously used for a photosensitive member for electronic photograph, a planar light emitting member such as a flat panel display of wall televisions, a back light of copiers, printers and liquid crystal displays, a light source for instruments, a display panel, a marking light and an accessory.

The present invention will be described more specifically with reference to examples in the following. However, the present invention is not limited to the examples.

The triplet energy gap and the singlet energy gap of a compound were measured in accordance with the following methods.

(1) Measurement of the Triplet Energy Gap

The lowest excited triplet energy level T1 was measured. The phosphorescence spectrum of a sample was measured (10 µmoles/liter; an EPA (diethyl ether:isopentane:ethanol=5:5:2 by volume) solution; 77K; a quartz cell; FLUO-ROLOG II manufactured by SPEX Company). A tangent was drawn to the increasing line at the short wavelength side of the phosphorescence spectrum and the wavelength at the intersection of the tangent and the abscissa (the end of light emission) was obtained. The obtained wavelength was converted into the energy.

(2) Measurement of the Singlet Energy Gap

The excited singlet energy gap was measured. Using a toluene solution ($10^{-5}$ moles/liter) of a sample, the absorption spectrum was obtained by a spectrometer for absorption of ultraviolet and visible light manufactured by HITACHI Co. Ltd. A tangent was drawn to the increasing line at the long wavelength side of the spectrum and the wavelength at the intersection of the tangent and the abscissa (the end of absorption) was obtained. The obtained wavelength was converted into the energy.

SYNTHESIS EXAMPLE 1

Synthesis of Compound (A5)

The route of synthesis of Compound (A5) is shown in the following.

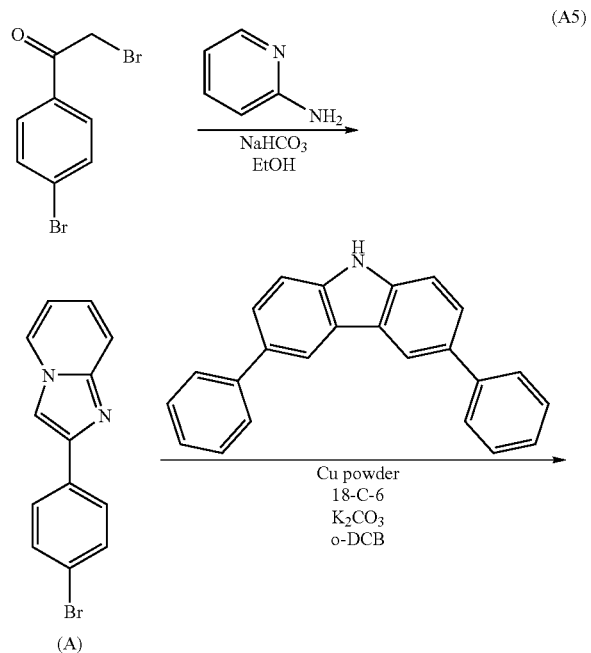

(1) Synthesis of Intermediate Compound (A)

2,4'-Dibromoacetophenone in an amount of 15 g (54 mmoles) was dissolved into 100 ml of ethanol. To the obtained solution, 7.0 g of sodium hydrogencarbonate and 5.2 g (55 mmoles) of 2-aminopyridine were added and the resultant mixture was heated for 9 hours under the refluxing condition. After the reaction was completed, the mixture was cooled at the room temperature. The formed crystals were separated by filtration and washed with water and ethanol and 12.5 g (the yield: 85%) of Intermediate Compound (A) was obtained.

(2) Synthesis of Compound (A5)

Into a reactor, 6.1 g (19 mmoles) of 3,6-diphenylcarbazole, 6.3 g (23 mmoles) of Intermediate Compound (A), 0.2 g of copper powder, 1.7 g of 18-crown-6 and 2.9 g (21 mmoles) of potassium carbonate were placed and 30 ml of o-dichlorobenzene was added as the solvent. The resultant mixture was heated at 200° C. in a silicone oil bath under a nitrogen stream and the reaction was allowed to proceed for 48 hours. After the reaction was completed, the reaction mixture was filtered under suction before being cooled and the obtained filtrate was concentrated using an evaporator. To the obtained oily product, 30 ml of methanol was added. The formed solid substance was separated by filtration under a reduced pressure and a gray solid substance was obtained. The obtained solid substance was recrystallized from benzene and 3.0 g (the yield: 31%) of white crystals were obtained. It was confirmed by 90 MHz $^1$H-NMR and FD-MS (the field desorption mass analysis) that the obtained crystals were the target substance (A5). The result of the measurement by FD-MS is shown in the following:

FD-MS calcd. for $C_{37}H_{25}N_3$=511; found: m/z=511 (M$^+$, 100)

The values of the energy gaps were obtained in accordance with the methods described above and the results are shown in Table 3.

SYNTHESIS EXAMPLE 2

Synthesis of Compound (A3)

The route of synthesis of Compound (A3) is shown in the following.

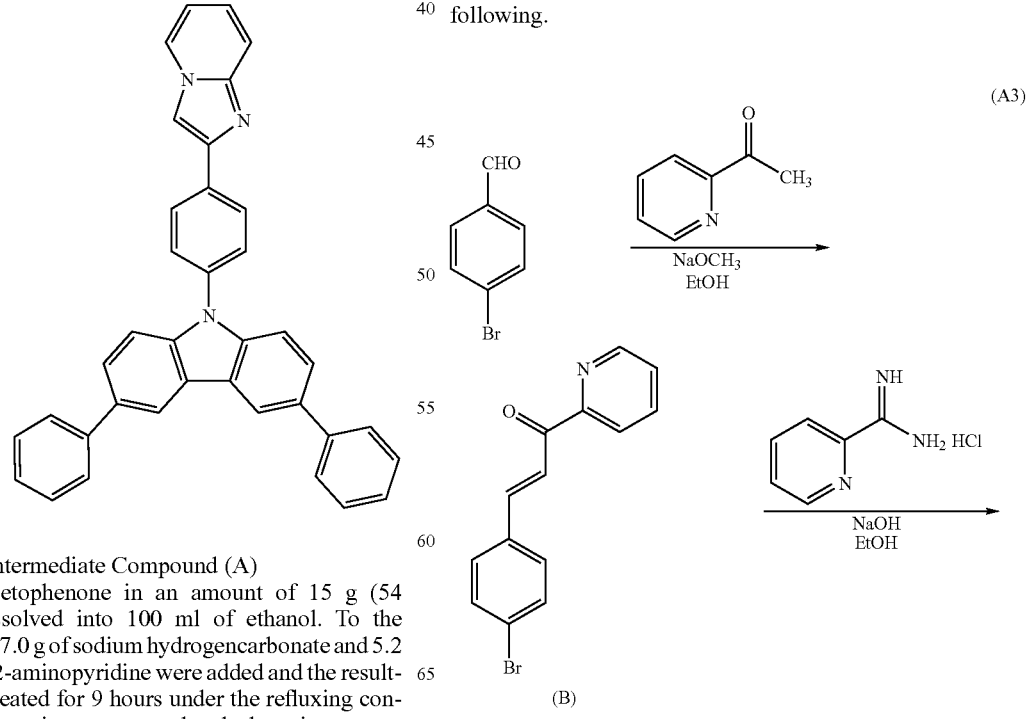

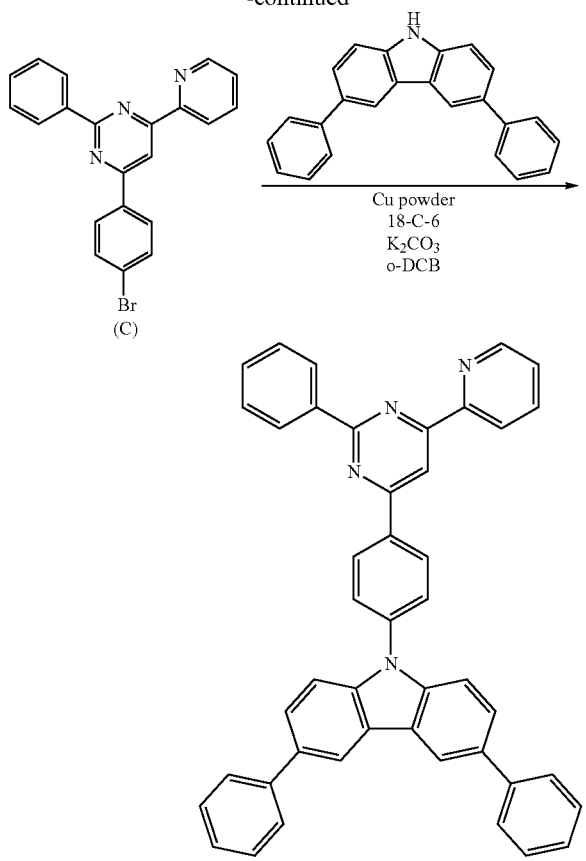

(1) Synthesis of Intermediate Compound (B)

4-Bromobenzaldehyde in an amount of 15 g (81 mmoles) was dissolved into 300 ml of ethanol. To the obtained solution, 10 g (83 mmoles) of 2-acetylpyridine and 15 g (81 mmoles) of a 28% methanol solution of sodium methoxide were added and the resultant mixture was stirred at the room temperature for 7 hours. After the reaction was completed, the formed crystals were separated by filtration and washed with ethanol and 9.5 g (the yield: 41%) of Intermediate Compound (B) was obtained.

(2) Synthesis of Intermediate Compound (C)

Intermediate Compound (B) in an amount of 9.5 g (33 mmoles) was dissolved into 80 ml of ethanol. To the obtained solution, 5.2 g (34 mmoles) of benzamidine hydrochloride and 2.6 g (65 mmoles) of sodium hydroxide were added and the resultant mixture was heated for 15 hours under the refluxing condition. After the reaction was completed, the mixture was cooled at the room temperature. The formed crystals were separated by filtration and washed with water and ethanol and 3.46 g (the yield: 27%) of Intermediate Compound (C) was obtained.

(3) Synthesis of Compound (A3)

Into a reactor, 6.1 g (19 mmoles) of 3,6-diphenylcarbazole, 8.9 g (23 mmoles) of Intermediate Compound (C), 0.2 g of copper powder, 1.7 g of 18-crown-6 and 2.9 g (21 mmoles) of potassium carbonate were placed and 30 ml of o-dichlorobenzene was added as the solvent. The resultant mixture was heated at 200° C. in a silicone oil bath under a nitrogen stream and the reaction was allowed to proceed for 48 hours. After the reaction was completed, the reaction mixture was filtered under suction before being cooled and the obtained filtrate was concentrated using an evaporator. To the obtained oily product, 30 ml of methanol was added. The formed solid substance was separated by filtration under a reduced pressure and a gray solid substance was obtained. The obtained solid substance was recrystallized from benzene and 3.9 g (the yield: 33%) of white crystals were obtained. It was confirmed by 90 MHz $^1$H-NMR and FD-MS that the obtained crystals were the target substance (A3). The result of the measurement by FD-MS is shown in the following:

FD-MS calcd. for $C_{45}H_{30}N_4$=626; found: m/z=626 (M$^+$, 100)

The values of the energy gaps were obtained in accordance with the same methods as those in Synthesis Example 1 and the results are shown in Table 3.

SYNTHESIS EXAMPLE 3

Synthesis of Compound (A26)

The route of synthesis of Compound (A26) is shown in the following.

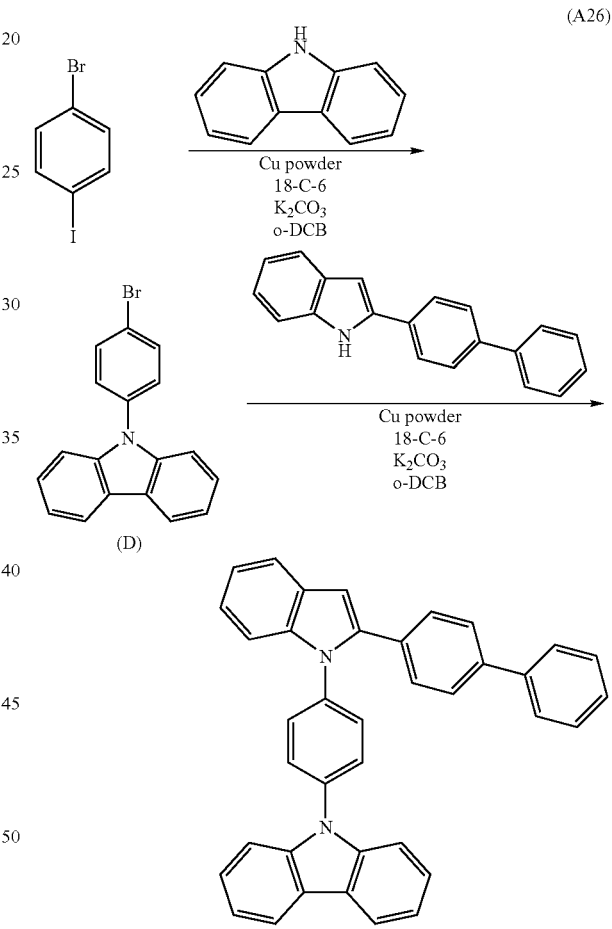

(A26)

(1) Synthesis of Intermediate Compound (D)

Into a reactor, 33 g (0.20 moles) of carbazole, 68 g (0.24 moles) of p-bromoiodobenzene, 2.0 g of copper powder, 18 g of 18-crown-6 and 30 g (0.22 moles) of potassium carbonate were placed and 300 ml of o-dichlorobenzene was added as the solvent. The resultant mixture was heated at 200° C. in a silicone oil bath under a nitrogen stream and the reaction was allowed to proceed for 24 hours. After the reaction was completed, the reaction mixture was filtered under suction using a Buchner funnel before being cooled and the obtained filtrate was concentrated using an evaporator. To the obtained oily product, 30 ml of methanol was added. The formed solid substance was separated by filtration under a reduced pressure and a gray solid substance was obtained. The obtained solid substance was recrystallized from benzene and 31 g (the yield: 49%) of white crystals were obtained.

(2) Synthesis of Compound (A26)

Into a reactor, 5.4 g (20 mmoles) of 2-biphenylindole, 7.7 g (24 mmoles) of Intermediate Compound (D), 0.2 g of copper powder, 1.8 g of 18-crown-6 and 3.0 g (22 mmoles) of potassium carbonate were placed and 30 ml of o-dichlorobenzene was added as the solvent. The resultant mixture was heated at 200° C. in a silicone oil bath under a nitrogen stream and the reaction was allowed to proceed for 48 hours. After the reaction was completed, the reaction mixture was filtered under suction before being cooled and the obtained filtrate was concentrated using an evaporator. To the obtained oily product, 30 ml of methanol was added. The formed solid substance was separated by filtration under a reduced pressure and a gray solid substance was obtained. The obtained solid substance was recrystallized from benzene and 1.7 g (the yield: 17%) of white crystals were obtained. It was confirmed by 90 MHz $^1$H-NMR and FD-MS that the obtained crystals were the target substance (A26). The result of the measurement by FD-MS is shown in the following:

FD-MS calcd. for $C_{38}H_{26}N_2$=510; found: m/z=510 (M$^+$, 100)

The values of the energy gaps were obtained in accordance with the same methods as those in Synthesis Example 1 and the results are shown in Table 3.

SYNTHESIS EXAMPLE 4

Synthesis of Compound (A27)

The route of synthesis of Compound (A27) is shown in the following.

In accordance with the same procedures as those conducted in Synthesis Example 3 (2) except that 2-biphenyl-3-phenylindole was used in place of 2-biphenylindole, 2.2 g (the yield: 19%) of white crystals were obtained. It was confirmed by 90 MHz $^1$H-NMR and FD-MS that the obtained crystals were the target substance (A27). The result of the measurement by FD-MS is shown in the following:

FD-MS calcd. for $C_{44}H_{30}N_2$=586; found: m/z=586 (M$^+$, 100)

The values of the energy gaps were obtained in accordance with the same methods as those in Synthesis Example 1 and the results are shown in Table 3.

SYNTHESIS EXAMPLE 5

Synthesis of Compound (A11)

The route of synthesis of Compound (A11) is shown in the following.

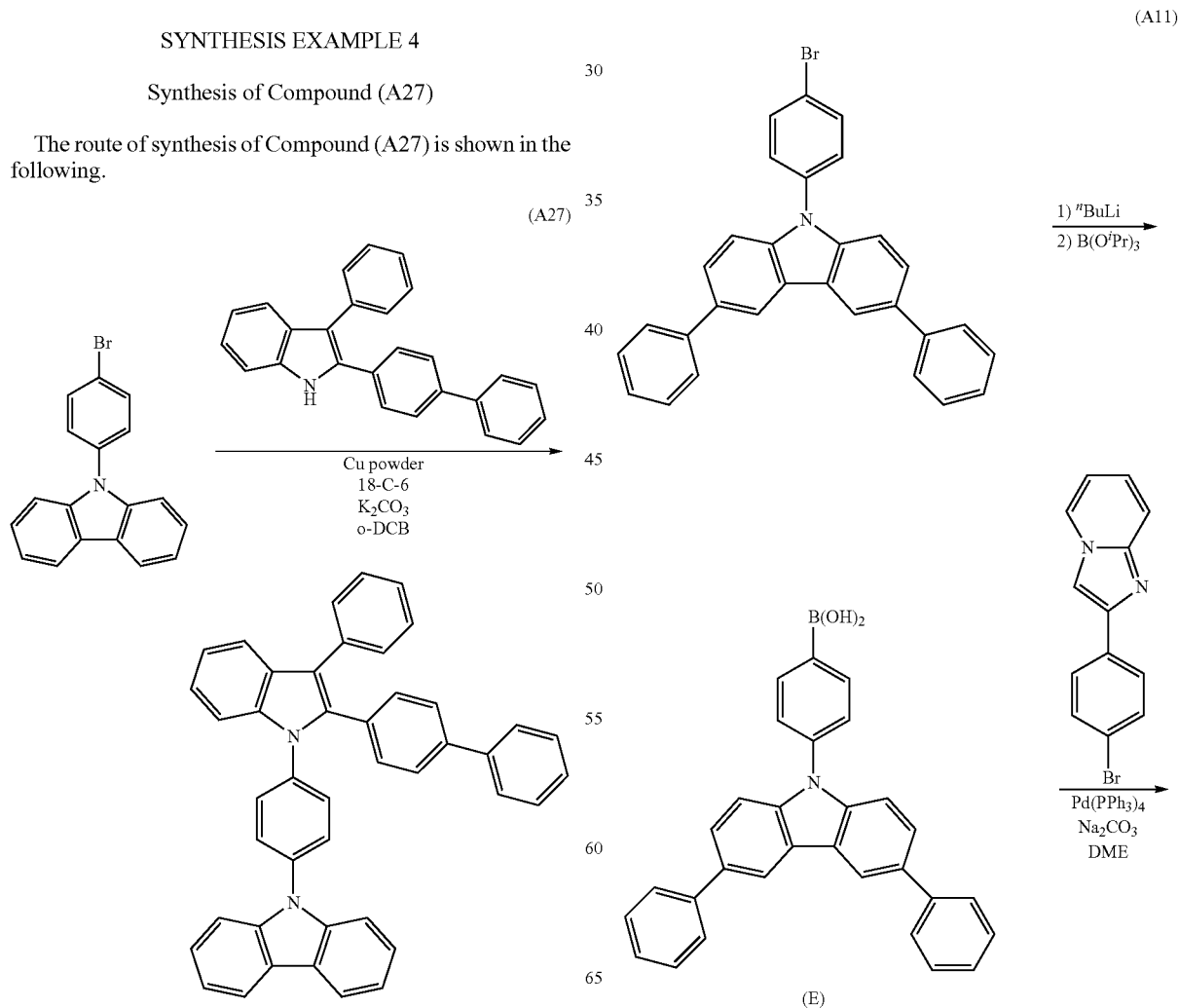

-continued

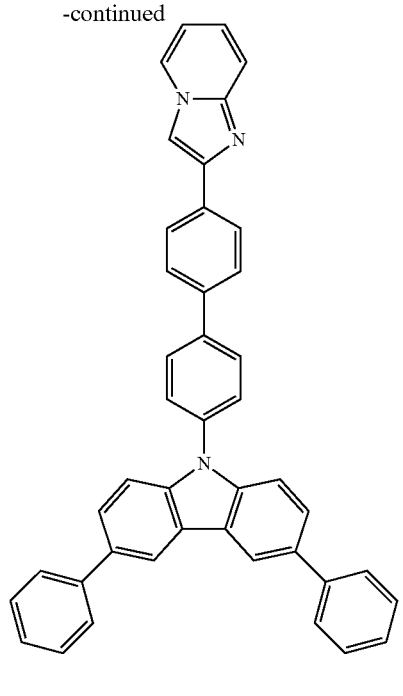

(1) Synthesis of Intermediate Compound (E)

3,6-Biphenyl-9-p-bromophenylcarbazole in an amount of 7.6 g (16 mmoles) was dissolved into 70 ml of ether. To the obtained solution, 12 ml of a hexane solution (1.6 M) of n-butyllithium was added at −60° C. After the resultant solution was stirred at a temperature between −60° C. and 0° C. for 2 hours, the solution was cooled at −60° C. again and a solution obtained by diluting 8.8 g of triisopropyl borate with 10 ml of ether was added dropwise. After the resultant mixture was stirred at a temperature between −60° C. and 0° C. for 2 hours, the reaction was quenched by adding a 5% aqueous solution of hydrochloric acid. The formed crystals were separated by filtration and washed with water and methanol and 4.0 g (the yield: 58%) of Intermediate Compound (E) was obtained.

(2) Synthesis of Compound (A11)

2-(4'-Bromophenyl)imidazo[1,2-a]pyridine in an amount of 2.0 g (7.3 mmoles), 3.5 g (8.0 mmoles) of Intermediate Compound (E), 0.2 g of copper powder and 0.17 g of tetrakis(triphenylphosphine)palladium were dissolved into 30 ml of 1,2-dimethoxyethane. To the resultant solution, 12 ml of a 2.0 M aqueous solution of sodium carbonate was added and the obtained solution was heated for 8 hours under the refluxing condition. After the reaction was completed, the formed solid substance was dissolved into dichloromethane, washed with water and dried with sodium sulfate. After the solvent was removed by distillation, the obtained product was washed with methanol and 2.0 g (the yield: 47%) of yellowish white solid substance was obtained. It was confirmed by 90 MHz $^1$H-NMR and FD-MS that the obtained solid substance was the target substance (A11). The result of the measurement by FD-MS is shown in the following:

FD-MS calcd. for $C_{43}H_{29}N_3$=587; found: m/z=587 (M$^+$, 100)

The values of the energy gaps were obtained in accordance with the same methods as those in Synthesis Example 1 and the results are shown in Table 3.

SYNTHESIS EXAMPLE 6

Synthesis of Compound (A9)

The route of synthesis of Compound (A9) is shown in the following.

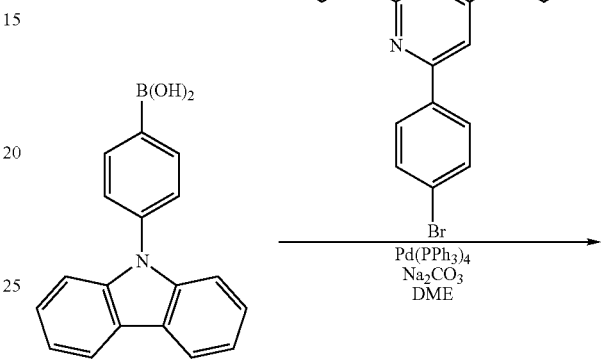

(A9)

Intermediate Compound (C) obtained in Synthesis Example 2 in an amount of 2.0 g (5.2 mmoles), 1.7 g (5.8 mmoles) of 4-(9'-carbazolyl)-phenylboric acid and 0.11 g of tetrakis(triphenylphosphine)palladium were dissolved into 20 ml of 1,2-dimethoxyethane. To the resultant solution, 9 ml of a 2.0 M aqueous solution of sodium carbonate was added and the obtained solution was heated for 8 hours under the refluxing condition. After the reaction was completed, the formed solid substance was dissolved into dichloromethane, washed with water and dried with sodium sulfate. After the solvent was removed by distillation, the obtained product was washed with methanol and 1.8 g (the yield: 62%) of yellowish white solid substance was obtained. It was confirmed by 90 MHz $^1$H-NMR and FD-MS that the obtained solid substance was the target substance (A9). The result of the measurement by FD-MS is shown in the following:

FD-MS calcd. for $C_{39}H_{26}N_4$=550; found: m/z=550 (M$^+$, 100)

The values of the energy gaps were obtained in accordance with the same methods as those in Synthesis Example 1 and the results are shown in Table 3.

SYNTHESIS EXAMPLE 7

Synthesis of Compound (A43)

The route of synthesis of Compound (A43) is shown in the following.

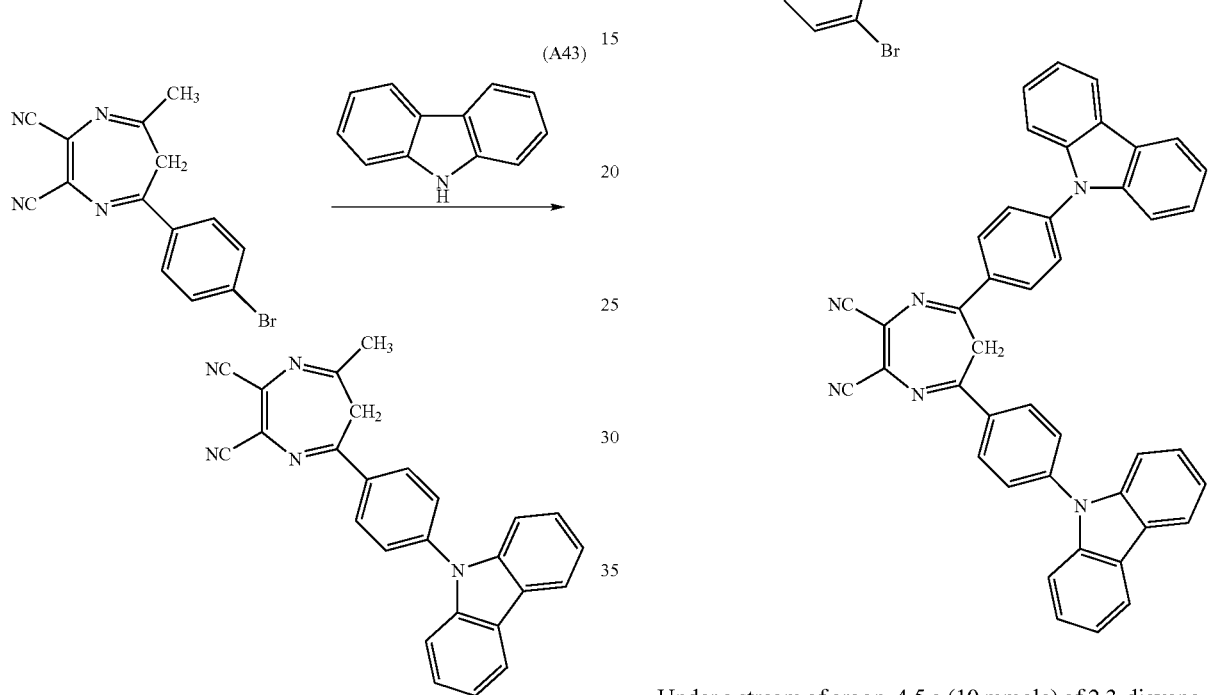

Under a stream of argon, 2.33 g (10 mmoles) of 2,3-dicyano-5-(p-bromophenyl)-7-methyl-6H-1,4-diazepine, 2 g (12 mmoles) of carbazole, 0.14 g (1.5% by mole) of tris(dibenzylideneacetone)dipalladium, 0.06 g (3% by mole) of tri-t-butylphosphine, 2.0 g (22 mmoles) of sodium t-butoxide and 100 ml of dry toluene were placed into a 200 ml three-necked flask equipped with a condenser and the resultant mixture was heated at 100° C. under stirring for one night. After the reaction was completed, the formed crystals were separated by filtration and washed with 100 ml of methanol and 1.2 g (3 mmoles) (the yield: 30%) of a light yellow powder was obtained. It was confirmed by the measurements of NMR, IR and FD-MS that the obtained powder was the target substance (A43). The result of the measurement by FD-MS is shown in the following:

FD-MS calcd. for $C_{26}H_{17}N_5$=399; found: m/z=399 (M$^+$, 100)

SYNTHESIS EXAMPLE 8

Synthesis of Compound (A45)

The route of synthesis of Compound (A45) is shown in the following.

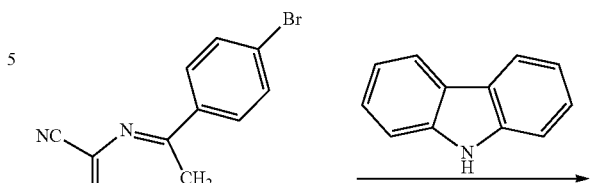

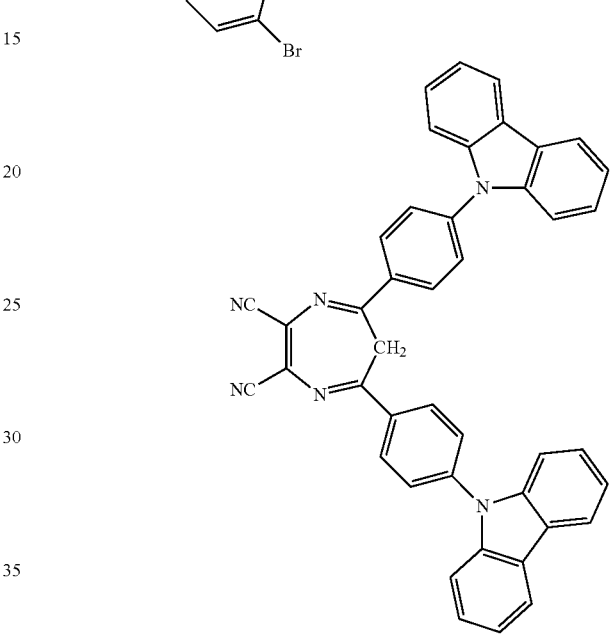

Under a stream of argon, 4.5 g (10 mmole) of 2,3-dicyano-5,7-bis(p-bromophenyl)-6H-1,4-diazepine, 4 g (24 mmoles) of carbazole, 0.28 g (1.5% by mole) of tris(dibenzylideneacetone)dipalladium, 0.12 g (3% by mole) of tri-t-butylphosphine, 4.2 g (442 mmoles) of sodium t-butoxide and 160 ml of dry toluene were placed into a 200 ml three-necked flask equipped with a condenser and the resultant mixture was heated at 100° C. under stirring for 18 hours. After the reaction was completed, the formed crystals were separated by filtration and washed with 100 ml of methanol and 1.8 g (2.9 mmoles) (the yield: 29%) of a white powder was obtained. It was confirmed by the measurements of NMR, IR and FD-MS that the obtained powder was the target substance (A45). The result of the measurement by FD-MS is shown in the following:

FD-MS calcd. for $C_{43}H_{26}N_6$=626; found: m/z=626 (M$^+$, 100)

SYNTHESIS EXAMPLE 9

Synthesis of Compound (B9)

The route of synthesis of Compound (B9) is shown in the following.

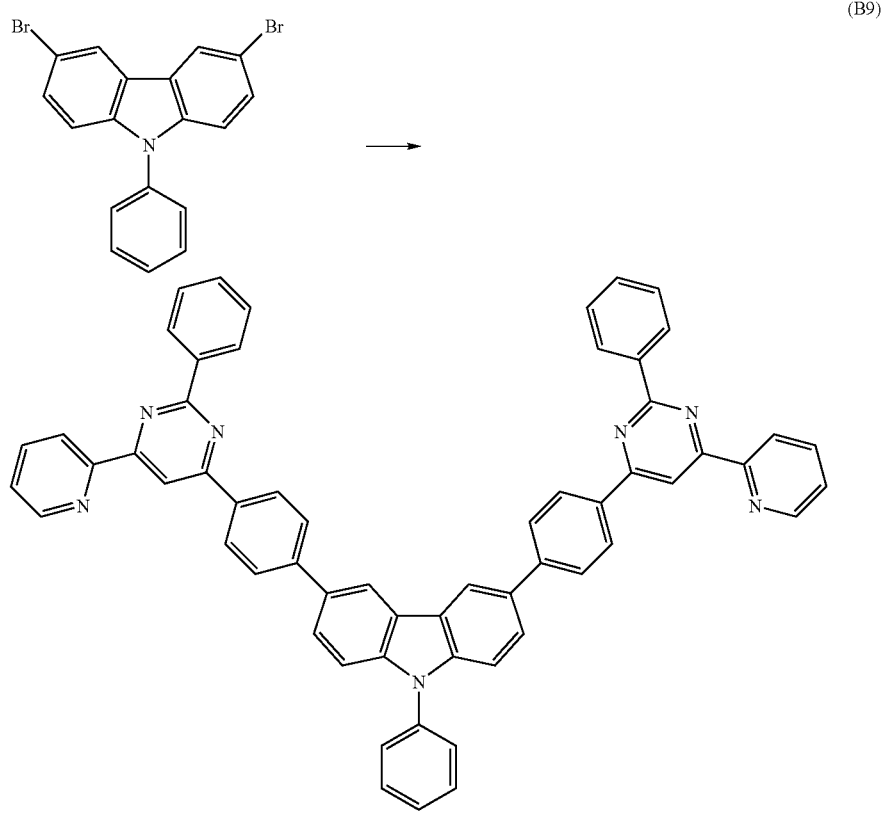

Under the atmosphere of argon, 11 g (32 mmole, 2.6 eq) of 4-(2'-phenyl-4'-pyridylpirimidin-6'-yl)phenylboric acid, 5 g (12 mmoles) of 3,6-dibromo-9-phenylcarbazole and 0.55 g (0.48 mmoles, 2% Pd) of tetrakis(triphenylphosphine)palladium(0) were suspended in 100 ml of 1,2-dimethoxyethane. To the resultant suspension, 10.2 g of a 2 M aqueous solution of sodium carbonate (96 mmoles, 3 eq/50 ml) was added and the resultant mixture was heated for 10 hours under the refluxing condition. After the organic layer was separated and concentrated, the product was purified in accordance with the column chromatography and 8.5 g (the yield: 83%) of a white solid substance was obtained. It was confirmed by 90 MHz $^1$H-NMR and FD-MS that the obtained solid substance was the target substance (B9). The result of the measurement by FD-MS is shown in the following:

FD-MS calcd. for $C_{60}H_{39}N_7$=857; found: m/z=857 (M$^+$, 100)

The values of the energy gaps were obtained in accordance with the same methods as those in Synthesis Example 1 and the results are shown in Table 3.

SYNTHESIS EXAMPLE 10

Synthesis of Compound (B11)

The route of synthesis of Compound (B11) is shown in the following.

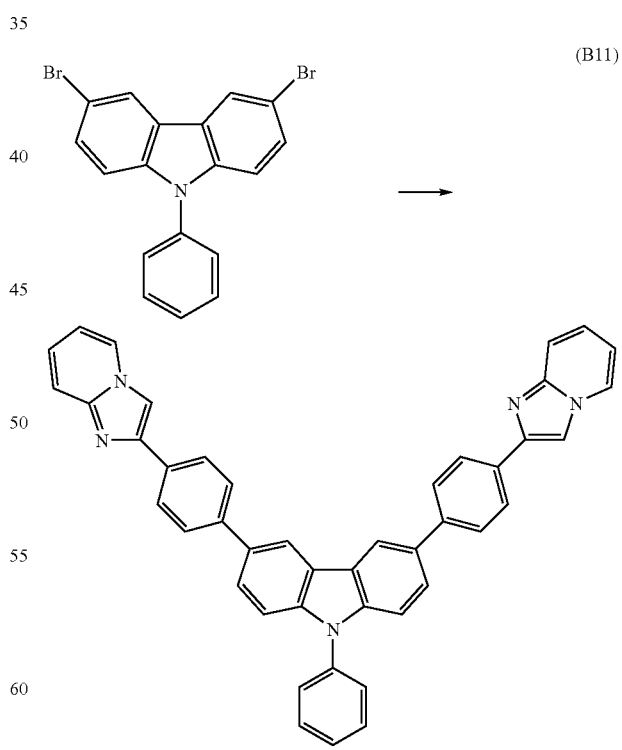

Under the atmosphere of argon, 7.6 g (32 mmole, 2.6 eq) of 4-(imidazopyridin-2'-yl)phenylboric acid, 5 g (12 mmoles) of 3,6-dibromo-9-phenylcarbazole and 0.55 g (0.48 mmoles, 2% Pd) of tetrakis(triphenylphosphine)palladium(0) were suspended in 100 ml of 1,2-dimethoxyethane. To the resultant suspension, 10.2 g of a 2 M aqueous solution of sodium carbonate (96 mmoles, 3 eq/50 ml) was added and the resultant mixture was heated for 10 hours under the refluxing condition. After the organic layer was separated and concentrated, the product was purified in accordance with the column chromatography and 5.7 g (the yield: 76%) of a white solid substance was obtained. It was confirmed by 90 MHz $^1$H-NMR and FD-MS that the obtained solid substance was the target substance (B11). The result of the measurement by FD-MS is shown in the following:

FD-MS calcd. for $C_{44}H_{29}N_5$=627; found: m/z=627 (M$^+$, 100)

The values of the energy gaps were obtained in accordance with the same methods as those in Synthesis Example 1 and the results are shown in Table 3.

SYNTHESIS EXAMPLE 11

Synthesis of Compound (A72)

The route of synthesis of Compound (A72) is shown in the following.

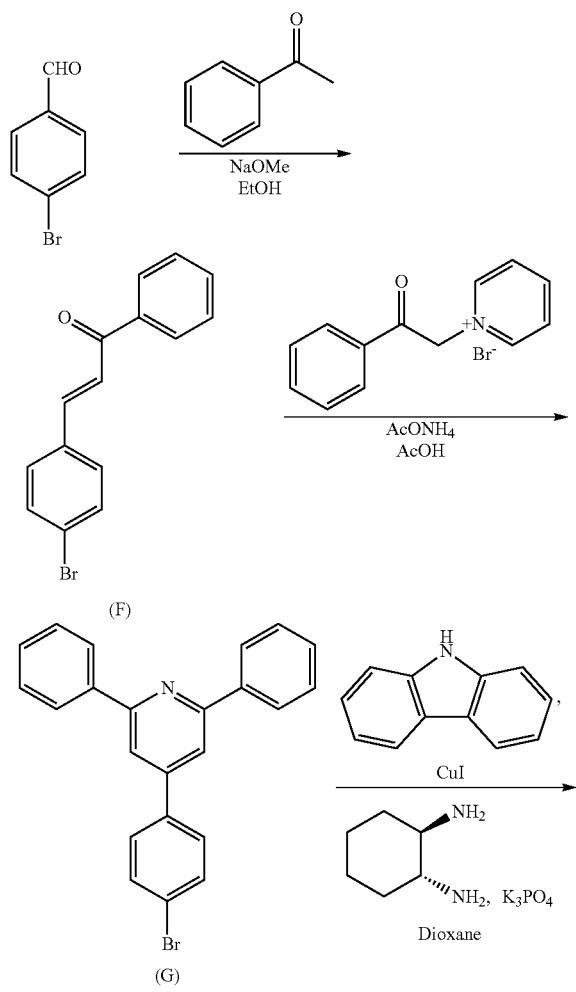

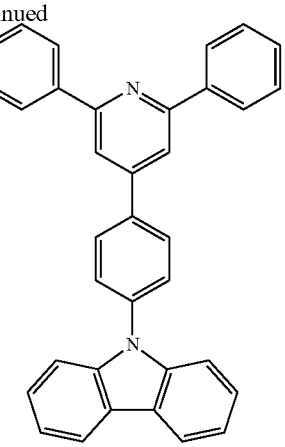

(1) Synthesis of Intermediate Compound (F)

In accordance with the same procedures as those conducted in Synthesis Example 2 (1) except that acetophenone was used in place of 2-acetylpyridine, 29.4 g (the yield: 84%) of Intermediate Compound (F) was obtained.

(2) Synthesis of Intermediate Compound (G)

Intermediate Compound (F) in an amount of 9.0 g (31 mmoles), 8.7 g (31 mmoles) of 1-phenylpyridinium bromide and 19.3 g (250 mmoles) of ammonium acetate were suspended into 27 ml of acetic acid and the resultant suspension was heated for 12 hours under the refluxing condition. The reaction solution was then cooled at the room temperature. Toluene and water were added and the resultant mixture was separated into two layers. The organic layer was washed with a 10% aqueous solution of sodium hydroxide and a saturated aqueous solution of sodium chloride, successively, and dried with anhydrous sodium sulfate. After the organic solvent was removed by distillation under a reduced pressure, 27 ml of ethanol was added. The formed crystals were separated by filtration and washed with ethanol and 10.6 g (the yield: 88%) of Intermediate Compound (G) was obtained.

(3) Synthesis of Compound (A72)

Intermediate Compound (G) in an amount of 3.5 g (9 mmoles), 1.7 g (10 mmoles) of carbazole, 0.09 g (0.5 mmoles) of copper iodide and 4.0 g (19 mmoles) of potassium phosphate were suspended into 18 ml of 1,4-dioxane. To the obtained suspension, 0.5 ml (4 mmoles) of trans-1,2-cyclohexanediamine was added. Under the atmosphere of argon, the resultant mixture was heated for 18 hours under the refluxing condition. The reaction solution was then cooled at the room temperature. Methylene chloride and water were added and the resultant mixture was separated into two layers. The organic layer was washed with a 5% aqueous solution of hydrochloric acid and water, successively, and dried with anhydrous sodium sulfate. After the organic solvent was removed by distillation, 15 ml of ethyl acetate was added. The formed crystals were separated by filtration and washed with ethyl acetate and 3.5 g (the yield: 83%) of yellowish white crystals were obtained. It was confirmed by 90 MHz $^1$H-NMR and FD-MS that the obtained crystals were the target substance (A72). The result of the measurement by FD-MS is shown in the following:

FD-MS calcd. for $C_{35}H_{24}N_2$=472; found: m/z=472 (M$^+$, 100)

The values of the energy gaps were obtained in accordance with the same methods as those in Synthesis Example 1 and the results are shown in Table 3.

SYNTHESIS EXAMPLE 12

Synthesis of Compound (A73)

The route of synthesis of Compound (A73) is shown in the following.

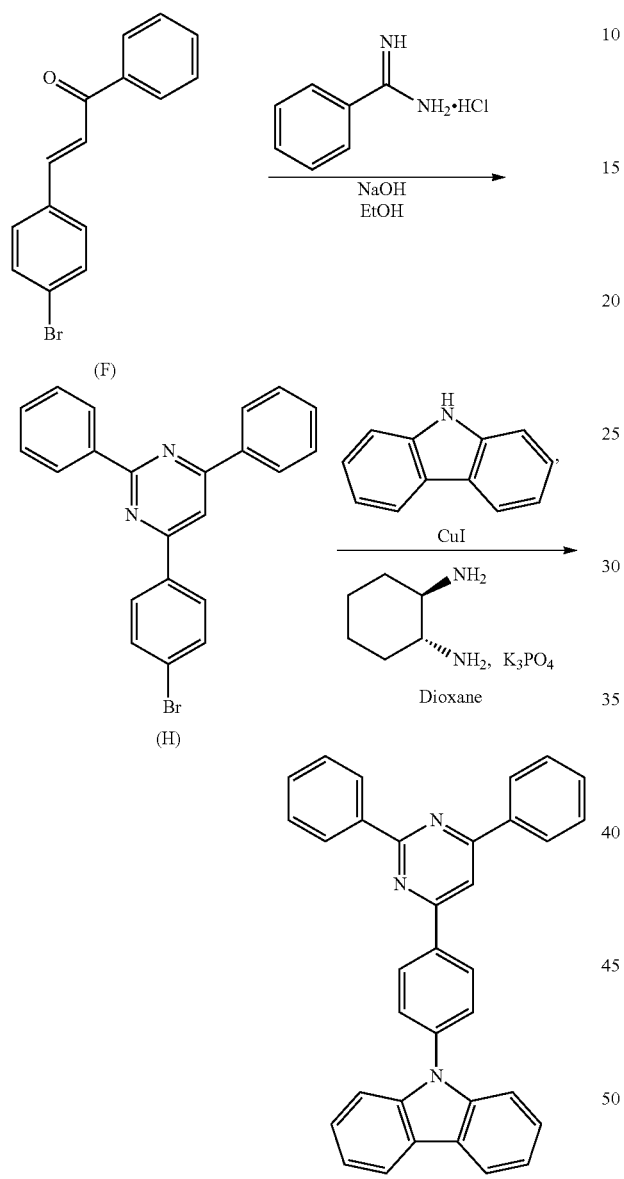

(1) Synthesis of Intermediate Compound (H)

In accordance with the same procedures as those conducted in Synthesis Example 2 (2) except that Intermediate Compound (F) obtained in Synthesis Example 11 was used in place of Intermediate Compound (B), 7.8 g (the yield: 61%) of Intermediate Compound (H) was obtained.

(2) Synthesis of Compound (A73)

In accordance with the same procedures as those conducted in Synthesis Example 11 (3) except that Intermediate Compound (H) was used in place of Intermediate Compound (G), 3.3 g (the yield: 76%) of yellowish white crystals were obtained. It was confirmed by 90 MHz $^1$H-NMR and FD-MS that the obtained crystals were the target substance (A73). The result of the measurement by FD-MS is shown in the following:

FD-MS calcd. for $C_{34}H_{23}N_3$=473; found: m/z=473 (M$^+$, 100)

The values of the energy gaps were obtained in accordance with the same methods as those in Synthesis Example 1 and the results are shown in Table 3.

SYNTHESIS EXAMPLE 13

Synthesis of Compound (A113)

The route of synthesis of Compound (A113) is shown in the following.

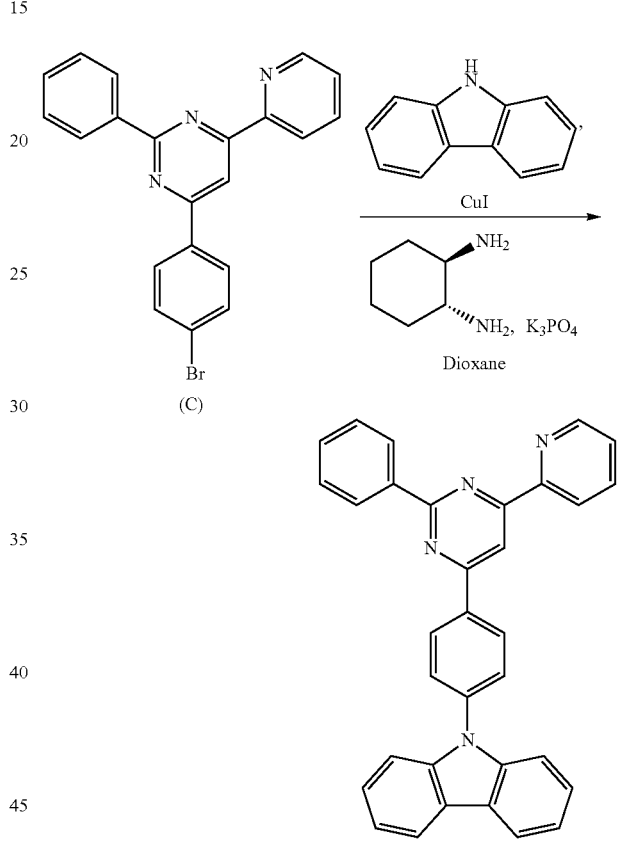

In accordance with the same procedures as those conducted in Synthesis Example 11 (3) except that Intermediate Compound (C) obtained in Synthesis Example 2 was used in place of Intermediate Compound (G), 1.5 g (the yield: 50%) of yellowish white crystals were obtained. It was confirmed by 90 MHz $^1$H-NMR and FD-MS that the obtained crystals were the target substance (A113). The result of the measurement by FD-MS is shown in the following:

FD-MS calcd. for $C_{33}H_{22}N_4$=474; found: m/z=474 (M$^+$, 100)

The values of the energy gaps were obtained in accordance with the same methods as those in Synthesis Example 1 and the results are shown in Table 3.

SYNTHESIS EXAMPLE 14

Synthesis of Compound (A98)

The route of synthesis of Compound (A98) is shown in the following.

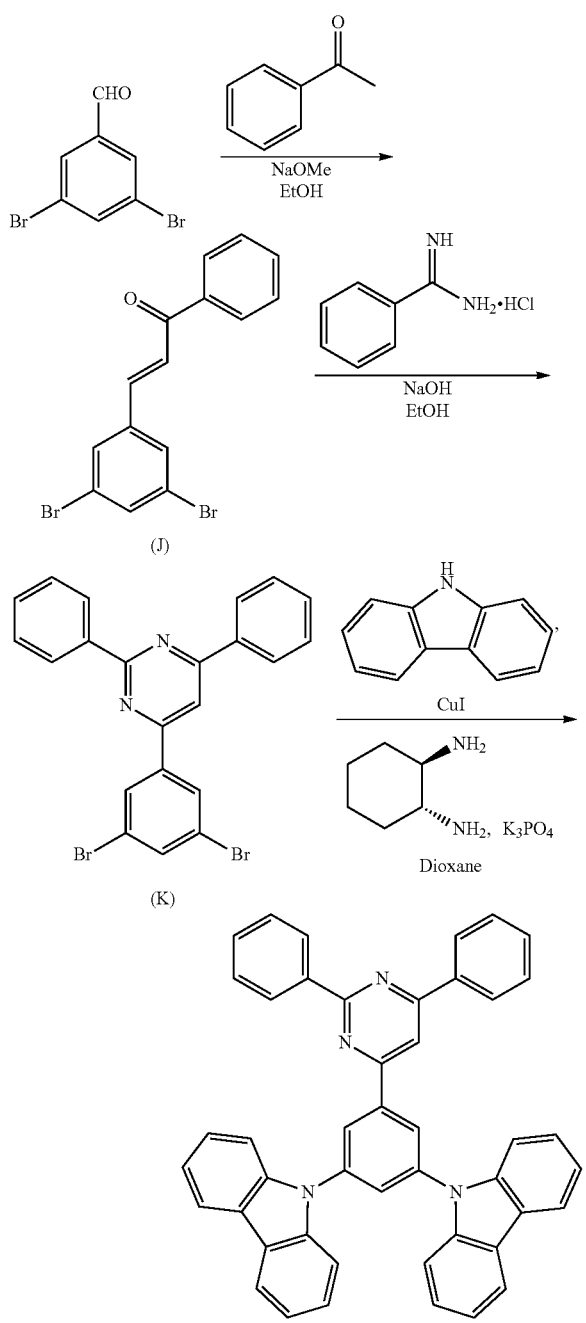

(1) Synthesis of Intermediate Compound (J)

In accordance with the same procedures as those conducted in Synthesis Example 2 (1) except that 3,5-dibromobenzaldehyde was used in place of 4-bromobenzaldehyde and acetophenone was used in place of 2-acetylpyridine, 19.2 g (the yield: 92%) of Intermediate Compound (J) was obtained.

(2) Synthesis of Intermediate Compound (K)

In accordance with the same procedures as those conducted in Synthesis Example 2 (2) except that Intermediate Compound (J) was used in place of Intermediate Compound (B), 5.5 g (the yield: 45%) of Intermediate Compound (K) was obtained.

(3) Synthesis of Compound (A98)

Intermediate Compound (K) in an amount of 3.0 g (6 mmoles), 2.3 g (14 mmoles) of carbazole, 0.12 g (0.6 mmoles) of copper iodide and 4.2 g (20 mmoles) of potassium phosphate were suspended into 21 ml of 1,4-dioxane. To the obtained suspension, 0.8 ml (6 mmoles) of trans-1,2-cyclohexanediamine was added. Under the atmosphere of argon, the resultant mixture was heated for 18 hours under the refluxing condition. The reaction solution was then cooled at the room temperature. Methylene chloride and water were added and the resultant mixture was separated into two layers. The organic layer was washed with water and dried with anhydrous sodium sulfate. After the organic solvent was removed by distillation under a reduced pressure, the residue of distillation was suspended into 21 ml of dioxane. To the obtained suspension, 0.12 g (0.6 mmoles) of copper iodide, 2.9 g (14 mmoles) of potassium phosphate and 0.8 ml (6 mmoles) of trans-1,2-cyclohexanediamine were added. Under the atmosphere of argon, the resultant mixture was heated for 18 hours under the refluxing condition. The reaction solution was then cooled at the room temperature. Methylene chloride and water were added and the resultant mixture was separated into two layers. The organic layer was washed with water and dried with anhydrous sodium sulfate. After the organic solvent was removed by distillation under a reduced pressure, 30 ml of ethyl acetate was added. The formed crystals were separated by filtration and washed with ethyl acetate and 3.3 g (the yield: 80%) of yellowish white crystals were obtained. It was confirmed by 90 MHz $^1$H-NMR and FD-MS that the obtained crystals were the target substance (A98). The result of the measurement by FD-MS is shown in the following:

FD-MS calcd. for $C_{46}H_{30}N_4$=638; found: m/z=638 (M$^+$, 100)

The values of the energy gaps were obtained in accordance with the same methods as those in Synthesis Example 1 and the results are shown in Table 3.

SYNTHESIS EXAMPLE 15

Synthesis of Compound (A105)

The route of synthesis of Compound (A105) is shown in the following.

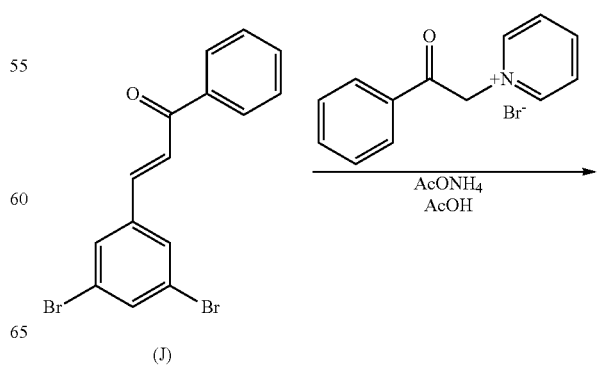

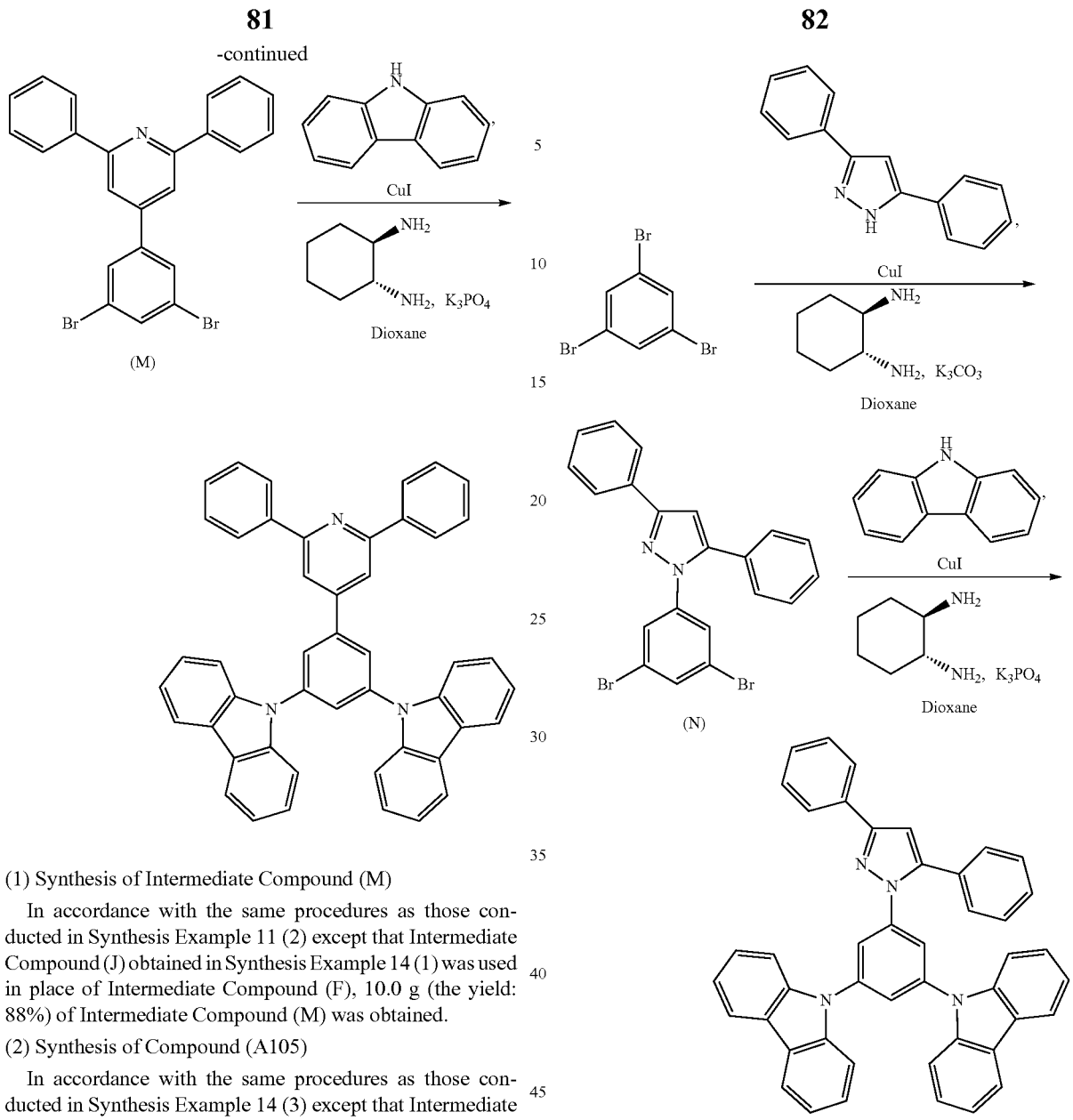

(1) Synthesis of Intermediate Compound (M)

In accordance with the same procedures as those conducted in Synthesis Example 11 (2) except that Intermediate Compound (J) obtained in Synthesis Example 14 (1) was used in place of Intermediate Compound (F), 10.0 g (the yield: 88%) of Intermediate Compound (M) was obtained.

(2) Synthesis of Compound (A105)

In accordance with the same procedures as those conducted in Synthesis Example 14 (3) except that Intermediate Compound (M) was used in place of Intermediate Compound (K), 2.9 g (the yield: 71%) of yellowish white crystals were obtained. It was confirmed by 90 MHz $^1$H-NMR and FD-MS that the obtained crystals were the target substance (A105). The result of the measurement by FD-MS is shown in the following:

FD-MS calcd. for $C_{47}H_{31}N_3$=637; found: m/z=637 (M$^+$, 100)

The values of the energy gaps were obtained in accordance with the same methods as those in Synthesis Example 1 and the results are shown in Table 3.

SYNTHESIS EXAMPLE 16

Synthesis of Compound (A108)

The route of synthesis of Compound (A108) is shown in the following.

(1) Synthesis of Intermediate Compound (N)

1,3,5-Tribromobenzene in an amount of 13.0 g (41 mmoles), 10.0 g (45 mmoles) of 3,5-diphenylpyrazole, 0.8 g (4 mmoles) of copper iodide and 11.9 g (86 mmoles) of potassium carbonate were suspended into 50 ml of 1,4-dioxane. To the obtained suspension, 4.9 ml (41 mmoles) of trans-1,2-cyclohexanediamine was added. Under the atmosphere of argon, the resultant mixture was heated for 18 hours under the refluxing condition. The reaction solution was then cooled at the room temperature. Methylene chloride and water were added and the resultant mixture was separated into two layers. The organic layer was washed with water and dried with anhydrous sodium sulfate. After the organic solvent was removed by distillation under a reduced pressure, the remaining product was purified in accordance with the silica gel column chromatography and 2.0 g (the yield: 11%) of Intermediate Compound (N) was obtained.

(2) Synthesis of Compound (A108)

Intermediate Compound (N) in an amount of 2.0 g (4 mmoles), 1.4 g (8 mmoles) of carbazole, 0.08 g (0.4 mmoles) of copper iodide and 2.9 g (14 mmoles) of potassium phosphate were suspended into 15 ml of 1,4-dioxane. To the obtained suspension, 0.5 ml (4 mmoles) of trans-1,2-cyclohexanediamine was added. Under the atmosphere of argon, the resultant mixture was heated for 18 hours under the refluxing condition. The reaction solution was then cooled at the room temperature. Methylene chloride and water were added and the resultant mixture was separated into two layers. The organic layer was washed with water and dried with anhydrous sodium sulfate. After the organic solvent was removed by distillation, the residue of distillation was suspended into 15 ml of 1,4-dioxane. To the obtained suspension, 0.08 g (0.4 mmoles) of copper iodide, 2.9 g (14 mmoles) of potassium phosphate and 0.5 ml (4 mmoles) of trans-1,2-cyclohexanediamine were added. Under the atmosphere of argon, the resultant mixture was heated for 14 hours under the refluxing condition. The reaction solution was then cooled at the room temperature. Methylene chloride and water were added and the resultant mixture was separated into two layers. The organic layer was washed with water and dried with anhydrous sodium sulfate. After the organic solvent was removed by distillation under a reduced pressure, 5 ml of ethanol and 15 ml of ethyl acetate were added. The formed crystals were separated by filtration and washed with a mixed solvent containing ethyl acetate and ethanol in relative amounts by volume of 5:2 and 2.4 g (the yield: 87%) of yellowish white crystals were obtained. It was confirmed by 90 MHz $^1$H-NMR and FD-MS that the obtained crystals were the target substance (A108). The result of the measurement by FD-MS is shown in the following:

FD-MS calcd. for $C_{45}H_{30}N_4$=626; found: m/z=626 (M$^+$, 100)

The values of the energy gaps were obtained in accordance with the same methods as those in Synthesis Example 1 and the results are shown in Table 3.

TABLE 3

| Compound | | Singlet energy gap (eV) | Triplet energy gap (eV) |
|---|---|---|---|
| Synthesis Example 1 | A5 | 3.2 | 2.7 |
| Synthesis Example 2 | A3 | 3.1 | 2.7 |
| Synthesis Example 3 | A26 | 3.1 | 2.6 |
| Synthesis Example 4 | A27 | 3.0 | 2.6 |
| Synthesis Example 5 | A11 | 3.0 | 2.7 |
| Synthesis Example 6 | A9 | 3.1 | 2.5 |
| Synthesis Example 9 | B9 | 3.2 | 2.6 |
| Synthesis Example 10 | B11 | 3.2 | 2.7 |
| Synthesis Example 11 | A72 | 3.5 | 2.8 |

TABLE 3-continued

| Compound | | Singlet energy gap (eV) | Triplet energy gap (eV) |
|---|---|---|---|
| Synthesis Example 12 | A73 | 3.3 | 2.8 |
| Synthesis Example 13 | A113 | 3.2 | 2.7 |
| Synthesis Example 14 | A98 | 3.5 | 2.9 |
| Synthesis Example 15 | A105 | 3.4 | 2.9 |
| Synthesis Example 16 | A108 | 3.7 | 3.0 |

EXAMPLE 1

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of N,N'-bis(N,N'-diphenyl-4-aminophenyl)-N,N'-diphenyl-4,4'-diamino-1,1'-biphenyl (a film of TPD232) having a thickness of 60 nm was formed in a manner such that the formed film covered the transparent electrode. The formed film of TPD232 worked as the hole injecting layer. On the formed film of TPD232, a film of 4,4'-bis[N-(1-naphthyl)-N-phenylamino]biphenyl (a film of NPD) having a thickness of 20 nm was formed by vapor deposition. The formed film of NPD worked as the hole transporting layer. On the formed film of NPD, a film of the above Compound (A5) having a thickness of 40 nm was formed by vapor deposition. At the same time, Compound (D1) shown in the following was vapor deposited in an amount such that the ratio of the amounts by weight of Compound (A5) to Compound (Di) was 40:3. Compound (D1) is a light emitting compound having a singlet energy as low as 2.79 eV so that blue light is emitted. The formed mixed film of Compound (A5) and Compound (D1) worked as the light emitting layer. On the film formed above, a film of BAlq shown in the following (Me means methyl group) having a thickness of 20 nm was formed. The film of BAlq worked as the electron injecting layer. Thereafter, Li (the source of lithium: manufactured by SAES GETTERS Company) as the reducing dopant and Alq were binary vapor deposited and an Alq:Li film having a thickness of 10 nm was formed as the second electron injecting layer (the cathode). On the formed Alq:Li film, metallic aluminum was vapor deposited to form a metal cathode and an organic EL device was prepared.

When a direct current voltage of 5.0 V was applied to the organic EL device prepared above, blue light was emitted at a luminance of 150 cd/m$^2$ and an efficiency of the light emission of 6.3 cd/A. The chromatic coordinates were (0.14, 0.16) and the purity of color was excellent.

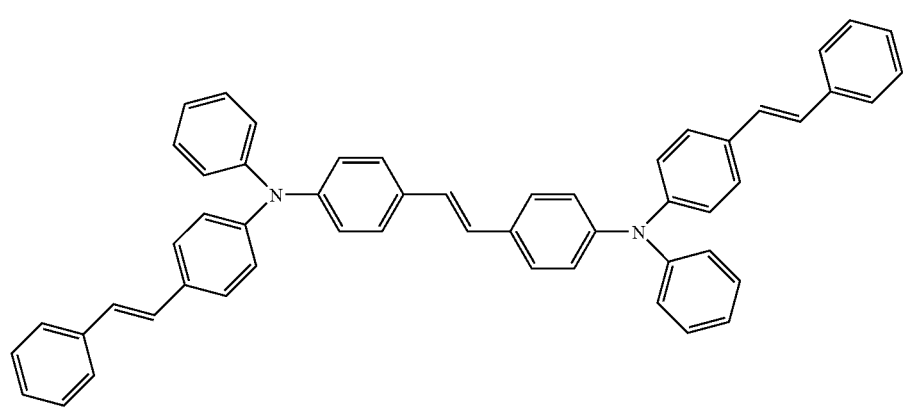

(D1)

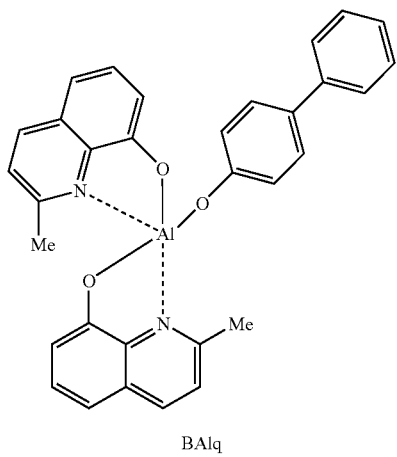

BAlq

EXAMPLES 2 TO 8

In accordance with the same procedures as those conducted in Example 1 except that compounds shown in Table 4 were used in place of Compound (A5), organic EL devices were prepared and the voltage of the direct current, the luminance of the emitted light, the efficiency of the light emission, the color of the emitted light and the purity of color were measured. The results are shown in Table 4.

COMPARATIVE EXAMPLE 1

In accordance with the same procedures as those conducted in Example 1 except that a conventional compound BCz shown in the following was used in place of Compound (A5), an organic EL device was prepared and the voltage of the direct current, the luminance of the emitted light, the efficiency of the light emission, the color of the emitted light and the purity of color were measured. The results are shown in Table 4.

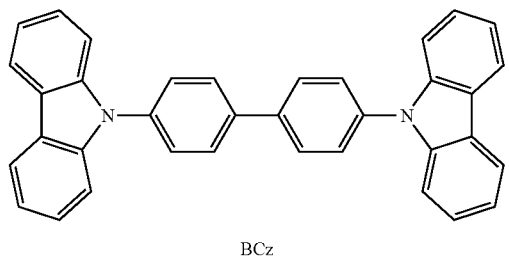 [SMILES: c1ccc2c(c1)c1ccccc1n2-c1ccc(-c2ccc(-n3c4ccccc4c4ccccc43)cc2)cc1]

BCz

COMPARATIVE EXAMPLE 2

In accordance with the same procedures as those conducted in Example 1 except that Compound (C2) shown in the following which is described in Japanese Patent Application Laid-Open No. 2001-288462 was used in place of Compound (A5), an organic EL device was prepared and the voltage of the direct current, the luminance of the emitted light, the efficiency of the light emission, the color of the emitted light and the purity of color were measured. The results are shown in Table 4.

TABLE 4

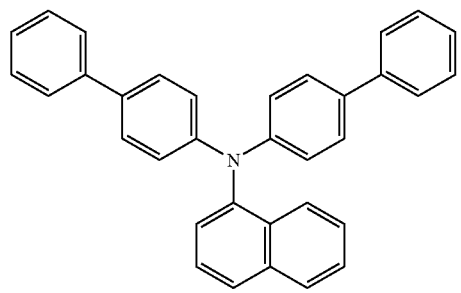 [SMILES: c1ccc(-c2ccc(N(c3ccc(-c4ccccc4)cc3)c3cccc4ccccc34)cc2)cc1]

(C2)

| | Organic host material of light emitting layer | Voltage (V) | Luminance of emitted light (cd/m$^2$) | Efficiency of light emission (cd/A) | Color of emitted light | Chromatic coordinates |
|---|---|---|---|---|---|---|
| Example 1 | A5 | 5.0 | 150 | 6.3 | blue | (0.14, 0.16) |
| Example 2 | A3 | 5.8 | 160 | 5.8 | blue | (0.15, 0.17) |
| Example 3 | A26 | 6.0 | 132 | 5.2 | blue | (0.14, 0.16) |
| Example 4 | A27 | 6.0 | 154 | 5.9 | blue | (0.14, 0.16) |
| Example 5 | A11 | 5.2 | 180 | 6.3 | blue | (0.15, 0.17) |

TABLE 4-continued (C2)

[Chemical structure of C2: triarylamine with two biphenyl groups and one naphthyl group]

| | Organic host material of light emitting layer | Voltage (V) | Luminance of emitted light (cd/m$^2$) | Efficiency of light emission (cd/A) | Color of emitted light | Chromatic coordinates |
|---|---|---|---|---|---|---|
| Example 6 | A9 | 6.2 | 145 | 5.1 | blue | (0.15, 0.16) |
| Example 7 | B9 | 5.7 | 151 | 5.7 | blue | (0.15, 0.17) |
| Example 8 | B11 | 5.0 | 181 | 6.9 | blue | (0.15. 0.17) |
| Comparative Example 1 | BCz | 8.5 | 70 | 2.4 | blue | (0.14, 0.16) |
| Comparative Example 2 | C2 | 6.5 | 65 | 2.6 | blue | (0.14, 0.16) |

As shown in Table, 4, in comparison with the organic EL devices using conventional compounds BCz and (C2) in Comparative Examples 1 and 2, respectively, the organic EL devices using the compounds of the present invention could be driven at lower voltages and emitted blue light in higher efficiencies. Since the energy gap of the compounds of the present invention is great, light emitting molecules having a great energy gap could be mixed into the light emitting layer and used for the light emission.

EXAMPLE 9

A glass substrate (manufactured by GEOMATEC Company) of 25 mm×75 mm×0.7 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of copper phthalocyanine shown in the following (a film of CuPc) having a thickness of 10 nm was formed in a manner such that the formed film covered the transparent electrode. The formed film of CuPc worked as the hole injecting layer. On the formed film of CuPc, a film of 1,1'-bis[4-N,N-di(p-tolyl)aminophenyl]cyclohexane (a film of TPAC) having a thickness of 30 nm was formed. The formed film of TPAC worked as the hole transporting layer. On the formed film of TPAC, a film of the above Compound (A72) having a thickness of 30 nm was formed by vapor deposition and the light emitting layer was formed. At the same time, Ir bis[(4,6-difluorophenyl)pyridinato-N,C$^{2'}$] picolinate (FIrpic shown in the following) as the phosphorescent Ir metal complex was added. The concentration of FIrpic in the light emitting layer was set at 7% by weight. This layer worked as the light emitting layer. On the film formed above, a film of Alq having a thickness of 30 nm was formed. The film of Alq worked as the electron injecting layer. Thereafter, LiF as the alkali metal halide was vapor deposited in an amount such that the formed film had a thickness of 0.2 nm and, then, aluminum was vapor deposited in an amount such that the formed film had a thickness of 150 nm. The formed film of Alq:Li film worked as the cathode. Thus, an organic EL device was prepared.

When the obtained device was tested by passing the electric current, bluish green light having a luminance of 89 cd/m$^2$ was emitted at a voltage of 6.6 V and a current density of 0.59 mA/cm$^2$. The chromatic coordinates were (0.18, 0.39) and the efficiency of the light emission was 14.98 cd/A.

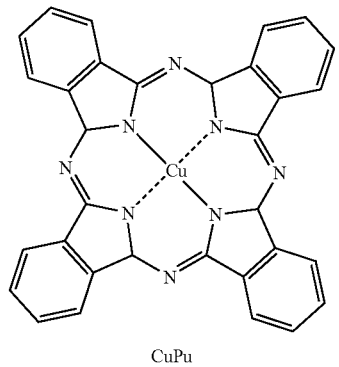

CuPu

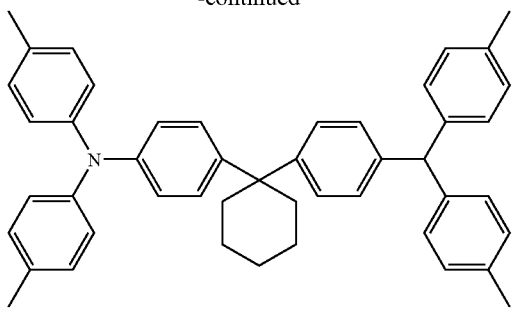

TPAC

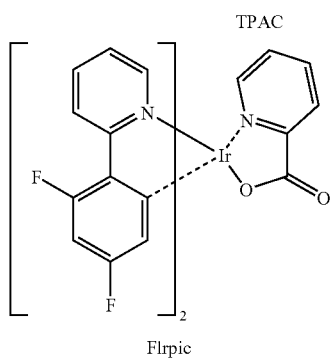

FIrpic

EXAMPLES 10 TO 12

In accordance with the same procedures as those conducted in Example 9 except that compounds shown in Table 5 were used in place of Compound (A72), organic EL devices were prepared and the voltage of the direct current, the current density, the luminance of the emitted light, the efficiency of the light emission, the color of the emitted light and the purity of color were measured. The results are shown in Table 5.

COMPARATIVE EXAMPLE 3

In accordance with the same procedures as those conducted in Example 9 except that the conventional compound BCz was used in place of Compound (A72), an organic EL device was prepared and the voltage of the direct current, the current density, the luminance of the emitted light, the efficiency of the light emission, the color of the emitted light and the purity of color were measured. The results are shown in Table 5.

COMPARATIVE EXAMPLE 4

In accordance with the same procedures as those conducted in Comparative Example 3 except that 4,4'-bis[N-(1-naphthyl)-N-phenylamino]biphenyl (α-NPD shown in the following) was used for the hole transporting layer in place of the compound TPAC and BAlq shown above was used for the electron transporting layer in place of the compound Alq, an organic EL device was prepared and the voltage of the direct current, the current density, the luminance of the emitted light, the efficiency of the light emission, the color of the emitted light and the purity of color were measured. The results are shown in Table 5.

TABLE 5

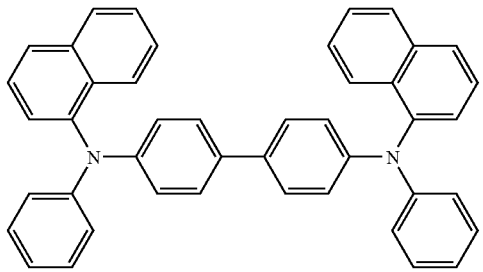

α-NPD

| | Organic host material of light emitting layer | Voltage (V) | Current density (mA/cm$^2$) | Luminance of emitted light (cd/m$^2$) | Efficiency of light emission (cd/A) | Color of emitted light | Chromatic coordinates |
|---|---|---|---|---|---|---|---|
| Example 9 | A72 | 6.6 | 0.59 | 89 | 14.98 | bluish green | (0.18, 0.39) |
| Example 10 | A98 | 6.4 | 0.54 | 86 | 15.89 | bluish green | (0.18, 0.40) |
| Example 11 | A105 | 6.9 | 0.84 | 99 | 11.76 | bluish green | (0.17, 0.40) |
| Example 12 | A73 | 6.0 | 1.00 | 99 | 9.91 | bluish green | (0.16, 0.39) |
| Comparative Example 3 | BCz | 7.8 | 1.70 | 98 | 5.80 | bluish green | (0.16, 0.37) |
| Comparative Example 4 | BCz | 7.6 | 1.09 | 99 | 9.15 | bluish green | (0.17, 0.37) |

As shown in Table 5, in comparison with the organic EL devices using the conventional compound BCz in Comparative Examples 3 and 4, the organic EL devices using the compounds of the present invention could be driven at a lower voltage and emit blue light at a higher efficiency. Since the energy gap of the compounds of the present invention is great, light emitting molecules having a great energy gap could be mixed into the light emitting layer and used for the light emission.

INDUSTRIAL APPLICABILITY

As described above in detail, by utilizing the material for organic electroluminescence devices comprising the compound represented by general formula (1) or (2) of the present invention, the organic electroluminescence device emitting blue light with a high efficiency of light emission and an excellent purity of color can be obtained. Therefore, the organic electroluminescence device of the present invention is very useful as the light source for various electronic instruments.

What is claimed is:

1. A material for organic electroluminescence devices which comprises a compound represented by following general formula (1):

wherein Cz represents a substituted or unsubstituted arylcarbazolyl group or carbazolylalkylene group, wherein the arylcarbazolyl group is bonded to A via the aryl portion of the arylcarbazolyl group or via the carbazolyl portion of the arylcarbazolyl group and A represents a group represented by following general formula (A):

wherein M represents an unsubstituted pyrimidine or a pyrimidine substituted with at least one group selected from the group consisting of a halogen atom, a carbazole group, a hydroxyl group, a substituted amino group, an unsubstituted amino group, a nitro group, a cyano group, a silyl group, a trifluoromethyl group, a carbonyl group, a carboxyl group, a substituted alkyl group, an unsubstituted alkyl group, a substituted alkenyl group, an unsubstituted alkenyl group, a substituted arylalkyl group, an unsubstituted arylalkyl group, an unsubstituted aromatic group, a substituted heteroaromatic heterocyclic group, a substituted aralkyl group, an unsubstituted aralkyl group, a substituted aryloxy group, an unsubstituted aryloxy group, a substituted alkyloxyl group and an unsubstituted alkyloxyl group, and wherein M' represents a substituted or unsubstituted heteroaromatic ring, wherein the heteroaromatic group is selected from the group consisting of a pyridine ring, a pyrimidine ring, a pyrazine ring, a triazine ring, an azaindolizine ring, an indolizine ring, an imidazole ring, an isoindole ring, an indazole ring, a purine ring, a pteridine ring, a β-carboline ring, a naphthyridine ring, a quinoxaline ring, a terpyridine ring, a bipyridine ring, an acridine ring, a phenanthroline ring, a phenazine ring, and an imidazopyridine ring, M and M' may represent a same ring or different rings, L represents a single bond, p represents an integer of 1 or 2, q represents an integer of 1, r represents an integer of 0 to 2; and n represents an integer of 1.

2. A material for organic electroluminescence devices according to claim 1, wherein p=2 and r=0 in formula (A).

3. A material for organic electroluminescence devices according to claim 1, wherein Cz represents a substituted or unsubstituted arylcarbazolyl group.

4. A material for organic electroluminescence devices according to claim 3, wherein Cz represents a substituted or unsubstituted phenylcarbazolyl group.

5. A material for organic electroluminescence devices according to Claim 3, wherein an aryl portion of the arylcarbazolyl group is substituted with carbazolyl group.

6. A material for organic electroluminescence devices according to claim 1, wherein a triplet energy gap of a compound represented by general formula (1) is 2.5 to 3.3 eV.

7. A material for organic electroluminescence devices according to claim 1, wherein a singlet energy gap of a compound represented by general formula (1) is 2.8 to 3.8 eV.

8. An organic electroluminescence device comprising an anode, a cathode and an organic thin film layer comprising at least one layer and disposed between the anode and the cathode, wherein at least one layer in the organic thin film layer comprises a material for organic electroluminescence devices described in claim 1.

9. An organic electroluminescence device according to claim 8, wherein the material for organic electroluminescence devices is an organic host material.

10. An organic electroluminescence device according to claim 8, which comprises an inorganic compound layer disposed between at least one of the electrodes and the organic thin film layer.

11. An organic electroluminescence device according to claim 8, which emits light by a multiplet excitation which is excitation to a triplet state or higher.

12. An organic electroluminescence device according to claim 8, which emits bluish light.

13. An organic electroluminescence device comprising an anode, a cathode and an organic thin film layer comprising at least one layer and disposed between the anode and the cathode, wherein a light emitting layer comprises a material for organic electroluminescence devices described in claim 1.

14. An organic electroluminescence device comprising an anode, a cathode and an organic thin film layer comprising at least one layer and disposed between the anode and the cathode, wherein an electron transporting layer comprises a material for organic electroluminescence devices described in claim 1.

15. An organic electroluminescence device comprising an anode, a cathode and an organic thin film layer comprising at least one layer disposed between the anode and the cathode, wherein a hole transporting layer comprises a material for organic electroluminescence devices described in claim 1.

16. A material for organic electroluminescence devices according to claim 1, wherein the heteroaromatic ring for M' has at least two nitrogen atoms as its ring members.

17. A material for organic electroluminescence devices according to claim 1, wherein the arylcarbazolyl group is N-bonded to A.

18. The material for organic electroluminescence devices according to claim 1, wherein the compound represented by formula (1) is at least one selected from the group consisting of:

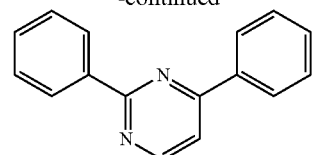

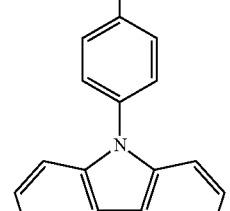

,

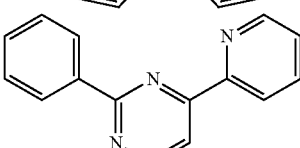

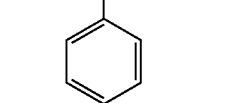

, and

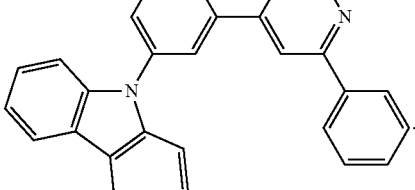

.

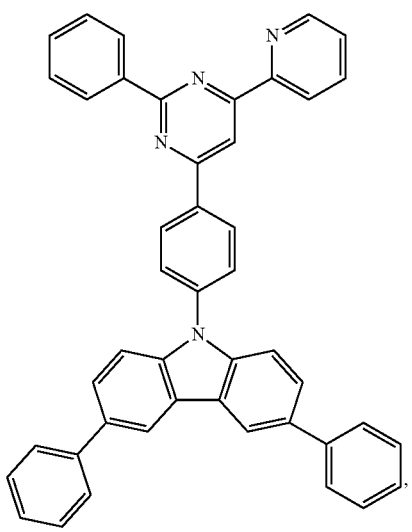

,

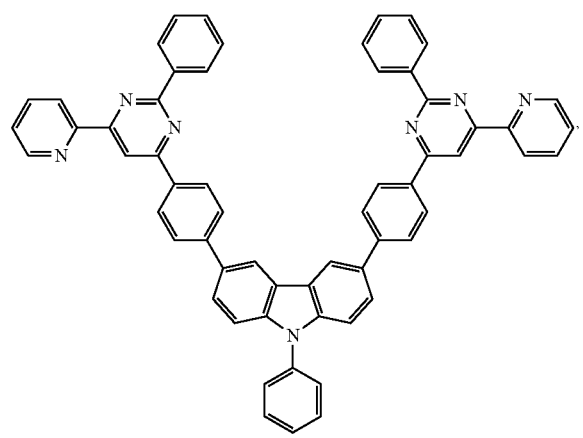

,

19. The material for organic electroluminescence devices according to claim 1, wherein the heteroaromatic ring for M' is selected from the group consisting of a pyridine ring, a pyrimidine ring, a triazine ring, an indolizine ring, a β-carboline ring, and an imidazopyridine ring.

20. The material for organic electroluminescence devices according to claim 1, wherein the heteroaromatic ring for M' is selected from the group consisting of a pyridine ring and a pyrimidine ring.

21. The material for organic electroluminescence devices according to claim 1, wherein the arylcarbazolyl group is bonded to A via the carbazolyl portion of the arylcarbazolyl group.

22. The material for organic electroluminescence according to claim 1, wherein r=1 or 2.

23. The material for organic electroluminescence devices according to claim 1, wherein p=2.

24. The material for organic electroluminescence devices according to claim 1, wherein the pyrimidine M is substituted with at least one group selected from the group consisting of a fluorine atom, a methyl group, a phenyl group, a naphthyl group, a pyridyl group, a pyrazyl group, a pyrimidyl group, an adamantyl group, a benzyl group, a cyano group and a silyl group.

25. The material for organic electroluminescence devices according to claim 1, wherein M is substituted with an unsubstituted aromatic group selected from the group consisting of a phenyl group, a naphthyl group, a biphenyl group, and an unsubstituted heteroaromatic heterocyclic group.

* * * * *